(12) United States Patent
Brain

(10) Patent No.: US 10,806,327 B2
(45) Date of Patent: Oct. 20, 2020

(54) LARYNGEAL MASK FOR USE WITH AN ENDOSCOPE

(71) Applicant: TELEFLEX LIFE SCIENCES PTE. LTD., Singapore (SG)

(72) Inventor: Archibald Ian Jeremy Brain, Victoria (SC)

(73) Assignee: TELEFLEX LIFE SCIENCES PTE, LTD., Singapore (SG)

( * ) Notice: Subject to any disclaimer, the term of this patent is extended or adjusted under 35 U.S.C. 154(b) by 236 days.

(21) Appl. No.: 14/359,557

(22) PCT Filed: Nov. 29, 2012

(86) PCT No.: PCT/GB2012/000876
§ 371 (c)(1),
(2) Date: May 20, 2014

(87) PCT Pub. No.: WO2013/079902
PCT Pub. Date: Jun. 6, 2013

(65) Prior Publication Data
US 2014/0323806 A1  Oct. 30, 2014

(30) Foreign Application Priority Data
Nov. 30, 2011  (GB) .................................. 1120628.1

(51) Int. Cl.
*A61B 1/00* (2006.01)
*A61B 1/273* (2006.01)
*A61M 16/04* (2006.01)

(52) U.S. Cl.
CPC ...... *A61B 1/00119* (2013.01); *A61B 1/00154* (2013.01); *A61B 1/2733* (2013.01);
(Continued)

(58) Field of Classification Search
CPC .............. A61M 16/04; A61M 16/0409; A61M 16/0415; A61M 16/0463; A61B 1/00154; A61B 1/2733
See application file for complete search history.

(56) References Cited

U.S. PATENT DOCUMENTS 2,096,831 A    10/1937  Wappler
2,099,127 A    11/1937  Leech
(Continued)

FOREIGN PATENT DOCUMENTS

AU    647437    6/1991
CA    2067782   11/1989
(Continued)

OTHER PUBLICATIONS

International Search Report for PCT/GB2006/001913, dated Aug. 28, 2006.
(Continued)

*Primary Examiner* — Kathryn E Ditmer
(74) *Attorney, Agent, or Firm* — BakerHostetler

(57) ABSTRACT

An endoscopy device for facilitating the use of an endoscope, comprising at least one airway tube and a mask carried at one end of the at least one airway rube, the mask having a distal end and a proximal end and a peripheral formation capable of conforming to, and of fitting within, the actual and potential space behind the larynx of the patient so as to form a seal around the circumference of the laryngeal inlet, the peripheral formation surrounding a hollow interior space or lumen of the mask and the at least one airway tube opening into the lumen of the mask, the device further comprising a conduit adapted for passage of an endoscope into the oesophagus of a patient when the mask is in place.

18 Claims, 27 Drawing Sheets

(52) U.S. Cl.
CPC .... *A61M 16/0409* (2014.02); *A61M 16/0415* (2014.02); *A61M 16/0445* (2014.02); *A61M 16/0431* (2014.02); *A61M 16/0486* (2014.02); *A61M 16/0493* (2014.02); *A61M 2205/0222* (2013.01); *A61M 2205/0238* (2013.01)

(56) References Cited

U.S. PATENT DOCUMENTS

| | | | |
|---|---|---|---|
| 2,252,874 A | 8/1941 | Vischer, Jr. | |
| 2,839,788 A | 6/1958 | Dembiak | |
| 2,862,498 A | 12/1958 | Weekes | |
| 3,124,959 A | 3/1964 | Pall et al. | |
| 3,529,596 A | 9/1970 | Garner | |
| 3,554,673 A | 1/1971 | Schwartz et al. | |
| 3,576,187 A | 4/1971 | Oddera | |
| 3,683,908 A | 8/1972 | Michael et al. | |
| 3,794,036 A | 2/1974 | Carroll | |
| 3,931,822 A | 1/1976 | Marici | |
| 3,948,273 A * | 4/1976 | Sanders | A61M 16/0463 128/207.15 |
| 4,056,104 A | 11/1977 | Jaffe | |
| 4,067,329 A | 1/1978 | Winicki et al. | |
| 4,096,759 A | 6/1978 | Desor | |
| 4,104,357 A | 8/1978 | Blair | |
| 4,116,201 A | 9/1978 | Shah | |
| 4,134,407 A | 1/1979 | Elam | |
| 4,159,722 A | 7/1979 | Walker | |
| 4,166,467 A | 9/1979 | Abramson | |
| 4,178,938 A | 12/1979 | Au et al. | |
| 4,178,940 A | 12/1979 | Au et al. | |
| 4,230,108 A * | 10/1980 | Young | A61M 16/04 128/207.15 |
| 4,231,365 A | 11/1980 | Scarberry | |
| 4,256,099 A | 3/1981 | Dryden | |
| 4,285,340 A | 8/1981 | Gezari et al. | |
| 4,338,930 A | 7/1982 | Williams | |
| 4,351,330 A | 9/1982 | Scarberry | |
| 4,363,320 A | 12/1982 | Kossove | |
| 4,445,366 A | 5/1984 | Gray | |
| 4,446,864 A | 5/1984 | Watson et al. | |
| 4,471,775 A | 9/1984 | Clair et al. | |
| 4,501,273 A | 2/1985 | McGinnis | |
| 4,509,514 A | 4/1985 | Brain et al. | |
| 4,510,273 A | 4/1985 | Miura et al. | |
| 4,526,196 A | 7/1985 | Pistillo | |
| 4,553,540 A | 11/1985 | Straith | |
| 4,583,917 A | 4/1986 | Shah | |
| 4,630,606 A | 12/1986 | Weerda et al. | |
| 4,689,041 A | 8/1987 | Corday et al. | |
| 4,700,700 A | 10/1987 | Eliachar | |
| 4,770,170 A | 9/1988 | Sato et al. | |
| 4,793,327 A | 12/1988 | Frankel | |
| 4,798,597 A | 1/1989 | Vaillancourt | |
| 4,825,862 A | 5/1989 | Sato | |
| 4,832,020 A | 5/1989 | Augustine | |
| 4,850,349 A | 7/1989 | Farahany | |
| 4,856,510 A | 8/1989 | Kowalewski et al. | |
| 4,872,483 A | 10/1989 | Shah | |
| 4,896,667 A | 1/1990 | Magnusson et al. | |
| 4,924,862 A | 5/1990 | Levinson | |
| 4,953,547 A | 9/1990 | Poole, Jr. | |
| 4,972,963 A | 11/1990 | Guarriello et al. | |
| 4,981,470 A | 1/1991 | Bombeck, IV | |
| 4,995,388 A | 2/1991 | Brain et al. | |
| 5,038,766 A | 8/1991 | Parker | |
| 5,042,469 A | 8/1991 | Augustine | |
| 5,042,476 A | 8/1991 | Smith | |
| 5,060,647 A | 10/1991 | Alessi | |
| 5,067,496 A | 11/1991 | Eisele | |
| 5,113,875 A | 5/1992 | Bennett | |
| 5,174,283 A | 12/1992 | Parker | |
| 5,203,320 A | 4/1993 | Augustine | |
| 5,218,970 A | 6/1993 | Turnbull et al. | |
| 5,235,973 A | 8/1993 | Levinson | |
| 5,237,988 A | 8/1993 | McNeese | |
| 5,241,325 A | 8/1993 | Nguyen et al. | |
| 5,241,956 A * | 9/1993 | Brain | A61M 16/0463 128/207.14 |
| 5,249,571 A | 10/1993 | Brain et al. | |
| 5,273,537 A | 12/1993 | Haskvitz et al. | |
| 5,277,178 A | 1/1994 | DinQiey et al. | |
| 5,282,464 A | 2/1994 | Brain et al. | |
| 5,297,547 A | 3/1994 | Brain et al. | |
| 5,303,697 A | 4/1994 | Brain et al. | |
| 5,305,743 A | 4/1994 | Brain | |
| 5,311,861 A | 5/1994 | Miller et al. | |
| 5,318,017 A | 6/1994 | Ellison | |
| 5,331,967 A | 7/1994 | Akerson et al. | |
| 5,339,805 A | 8/1994 | Parker | |
| 5,339,808 A | 8/1994 | Don Michael | |
| 5,355,879 A | 10/1994 | Brain et al. | |
| 5,361,753 A | 11/1994 | Pothmann et al. | |
| 5,391,248 A | 2/1995 | Brain et al. | |
| 5,400,771 A | 3/1995 | Pirak et al. | |
| 5,421,325 A | 6/1995 | Cinberg et al. | |
| 5,438,982 A | 8/1995 | Macintyre | |
| 5,443,063 A | 8/1995 | Greenberg | |
| 5,452,715 A | 9/1995 | Boussignac et al. | |
| 5,459,700 A | 10/1995 | Jacobs | |
| 5,487,383 A | 1/1996 | Levinson | |
| 5,529,582 A | 6/1996 | Fukuhara et al. | |
| 5,546,935 A | 8/1996 | Champeau | |
| 5,546,936 A | 8/1996 | Virag et al. | |
| 5,551,420 A | 9/1996 | Lurie et al. | |
| 5,554,673 A | 9/1996 | Shah | |
| 5,569,219 A | 10/1996 | Hakki et al. | |
| 5,577,693 A | 11/1996 | Corn | |
| 5,582,167 A | 12/1996 | Joseph | |
| 5,584,290 A | 12/1996 | Brain et al. | |
| 5,590,643 A | 1/1997 | Flam | |
| 5,599,301 A | 2/1997 | Jacobs et al. | |
| 5,623,921 A | 4/1997 | Kinsinger et al. | |
| 5,623,924 A | 4/1997 | Lindenman et al. | |
| 5,626,151 A | 5/1997 | Linden | |
| 5,632,271 A * | 5/1997 | Brain | A61M 16/04 128/207.14 |
| RE35,531 E | 6/1997 | Callaghan et al. | |
| 5,653,229 A | 8/1997 | Greenberg | |
| 5,655,528 A | 8/1997 | Pagan et al. | |
| 5,682,880 A | 11/1997 | Brain et al. | |
| 5,692,498 A | 12/1997 | Lurie et al. | |
| 5,694,929 A | 12/1997 | Christopher | |
| 5,711,293 A | 1/1998 | Brain et al. | |
| 5,738,094 A | 4/1998 | Hottman | |
| 5,743,254 A | 4/1998 | Parker | |
| 5,743,258 A | 4/1998 | Sato et al. | |
| 5,746,202 A | 5/1998 | Pagan et al. | |
| 5,771,889 A | 6/1998 | Pagan et al. | |
| 5,778,872 A | 7/1998 | Fukunaga et al. | |
| 5,791,341 A | 8/1998 | Bullard | |
| 5,794,617 A | 8/1998 | Brunell et al. | |
| 5,816,240 A | 10/1998 | Komesaroff | |
| 5,819,723 A | 10/1998 | Joseph | |
| 5,832,916 A | 11/1998 | Lundberg et al. | |
| 5,850,832 A | 12/1998 | Chu | |
| 5,855,203 A | 1/1999 | Matter | |
| 5,856,510 A | 1/1999 | Meng et al. | |
| 5,860,418 A | 1/1999 | Lundberg et al. | |
| 5,862,801 A | 1/1999 | Wells | |
| 5,865,176 A | 2/1999 | O'Neil et al. | |
| 5,878,745 A | 3/1999 | Brain et al. | |
| 5,881,726 A | 3/1999 | Neame | |
| 5,893,891 A | 4/1999 | Zahedi et al. | |
| 5,896,858 A | 4/1999 | Brain | |
| 5,915,383 A | 6/1999 | Pagan | |
| 5,921,239 A | 7/1999 | McCall et al. | |
| 5,924,862 A | 7/1999 | White | |
| 5,935,084 A | 8/1999 | Southworth | |
| 5,937,860 A | 8/1999 | Cook | |
| 5,957,133 A | 9/1999 | Hart | |
| 5,976,075 A | 11/1999 | Beane et al. | |
| 5,979,445 A | 11/1999 | Neame et al. | |
| 5,983,891 A | 11/1999 | Fukunaga | |
| 5,983,896 A | 11/1999 | Fukunaqa et al. | |

(56) References Cited

U.S. PATENT DOCUMENTS

| | | |
|---|---|---|
| 5,983,897 A | 11/1999 | Pagan |
| 5,988,167 A | 11/1999 | Kamen |
| 5,996,582 A | 12/1999 | Turnbull |
| 6,003,510 A | 12/1999 | Anunta |
| 6,003,511 A | 12/1999 | Fukunaga et al. |
| 6,003,514 A | 12/1999 | Pagan |
| 6,012,452 A | 1/2000 | Pagan |
| 6,021,779 A | 2/2000 | Paqan |
| 6,050,264 A | 4/2000 | Greenfield |
| 6,062,219 A | 5/2000 | Lurie et al. |
| 6,070,581 A | 6/2000 | Augustine et al. |
| 6,079,409 A | 6/2000 | Brain et al. |
| D429,811 S | 8/2000 | Bermudez et al. |
| 6,095,144 A | 8/2000 | Pagan |
| 6,098,621 A | 8/2000 | Esnouf et al. |
| 6,110,143 A | 8/2000 | Kamen |
| 6,116,243 A | 9/2000 | Pagan |
| 6,119,695 A | 9/2000 | Augustine et al. |
| 6,131,571 A | 10/2000 | Lamootang et al. |
| 6,149,603 A | 11/2000 | Parker |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald et al. |
| 6,315,739 B1 | 11/2001 | Merilainen et al. |
| 6,338,343 B1 | 1/2002 | Augustine et al. |
| 6,352,077 B1 | 3/2002 | Shah |
| 6,386,199 B1 | 5/2002 | Alfery |
| 6,390,093 B1 | 5/2002 | Mongeon |
| 6,422,239 B1 | 7/2002 | Cook |
| 6,427,686 B2 | 8/2002 | Augustine et al. |
| 6,439,232 B1 * | 8/2002 | Brain ............... A61M 16/04 128/200.26 |
| 6,450,164 B1 | 9/2002 | Banner et al. |
| 6,508,250 B1 | 1/2003 | Esnouf |
| 6,546,931 B2 | 4/2003 | Lin et al. |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |
| 6,766,801 B1 | 7/2004 | Wright |
| 6,955,645 B1 | 10/2005 | Zeitels |
| 7,004,169 B2 | 2/2006 | Brain et al. |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain et al. |
| 7,159,589 B2 | 1/2007 | Brain |
| RE39,938 E | 12/2007 | Brain |
| 7,383,736 B2 | 6/2008 | Esnouf |
| 7,694,682 B2 | 4/2010 | Petersen et al. |
| 7,895,497 B2 | 2/2011 | Pisek et al. |
| 7,997,274 B2 | 8/2011 | Baska |
| 8,033,176 B2 | 10/2011 | Esnouf |
| 8,413,658 B2 | 4/2013 | Williams |
| 9,078,559 B2 | 7/2015 | Tsunoda et al. |
| 2002/0026178 A1 | 2/2002 | Ouchi |
| 2003/0000534 A1 | 1/2003 | Alfery |
| 2003/0037790 A1 | 2/2003 | Brain |
| 2003/0051734 A1 | 3/2003 | Brain |
| 2003/0101998 A1 | 6/2003 | Zecca et al. |
| 2003/0131845 A1 | 7/2003 | Lin |
| 2003/0168062 A1 | 9/2003 | Blythe et al. |
| 2003/0172925 A1 | 9/2003 | Zecca et al. |
| 2003/0172935 A1 | 9/2003 | Miller |
| 2004/0020491 A1 * | 2/2004 | Fortuna ............. A61M 16/04 128/207.15 |
| 2004/0089307 A1 * | 5/2004 | Brain ............... A61M 16/04 128/207.14 |
| 2005/0066975 A1 | 3/2005 | Brain |
| 2005/0081861 A1 | 4/2005 | Nasir |
| 2005/0090712 A1 | 4/2005 | Cubb |
| 2005/0133037 A1 | 6/2005 | Russell |
| 2005/0139220 A1 | 6/2005 | Christopher |
| 2005/0178388 A1 | 8/2005 | Kuo |
| 2005/0199244 A1 | 9/2005 | Tateo et al. |
| 2005/0274383 A1 | 12/2005 | Brain |
| 2006/0124132 A1 | 6/2006 | Brain |
| 2006/0180156 A1 | 8/2006 | Baska |
| 2006/0201516 A1 | 9/2006 | Petersen et al. |
| 2006/0254596 A1 | 11/2006 | Brain |
| 2007/0017527 A1 * | 1/2007 | Totz ................ A61M 16/04 128/207.15 |
| 2007/0089754 A1 | 4/2007 | Jones |
| 2007/0240722 A1 | 10/2007 | Kessler |
| 2008/0041392 A1 | 2/2008 | Cook |
| 2008/0142017 A1 | 6/2008 | Brain |
| 2008/0276936 A1 | 11/2008 | Cook |
| 2008/0308109 A1 | 12/2008 | Brain |
| 2009/0090356 A1 | 4/2009 | Cook |
| 2009/0133701 A1 | 5/2009 | Brain |
| 2009/0139524 A1 | 6/2009 | Esnouf |
| 2009/0145438 A1 | 6/2009 | Brain |
| 2010/0059061 A1 | 3/2010 | Brain |
| 2010/0089393 A1 | 4/2010 | Brain |
| 2010/0211140 A1 | 8/2010 | Barbut et al. |
| 2010/0242957 A1 | 9/2010 | Fortuna |
| 2010/0249639 A1 * | 9/2010 | Bhatt ............... A61B 1/00082 600/546 |
| 2011/0023890 A1 | 2/2011 | Baska |
| 2011/0077466 A1 * | 3/2011 | Rosenthal ......... A61B 1/00045 600/188 |
| 2011/0220117 A1 * | 9/2011 | Dubach ............. A61M 16/04 128/207.14 |
| 2011/0226256 A1 | 9/2011 | Dubach |
| 2011/0245805 A1 | 10/2011 | Swinehart et al. |
| 2012/0085351 A1 | 4/2012 | Brain |
| 2012/0090609 A1 * | 4/2012 | Dubach ............. A61M 16/04 128/204.18 |
| 2012/0145161 A1 | 6/2012 | Brain |
| 2012/0174929 A1 | 7/2012 | Esnouf |
| 2012/0186510 A1 | 7/2012 | Esnouf |
| 2014/0034060 A1 | 2/2014 | Esnouf et al. |
| 2015/0209538 A1 | 7/2015 | Hansen |

FOREIGN PATENT DOCUMENTS

| | | |
|---|---|---|
| CA | 2141167 | 1/1994 |
| CA | 2012750 | 8/1999 |
| CN | 1166138 A | 11/1997 |
| CN | 2579352 Y | 10/2003 |
| CN | 1863568 A | 11/2006 |
| CN | 1863568 A | 11/2006 |
| CN | 2882657 Y | 3/2007 |
| CN | 101057994 A | 10/2007 |
| CN | 100531818 C | 8/2009 |
| CN | 201516220 U | 6/2010 |
| CN | 201684261 U | 12/2010 |
| CN | 201719659 U | 1/2011 |
| CN | 101991898 A | 3/2011 |
| CN | 102335478 A | 2/2012 |
| CN | 103221087 B | 7/2013 |
| DE | 2945662 A1 | 5/1981 |
| DE | 4447186 | 7/1996 |
| DE | 10042172 A1 | 4/2001 |
| EP | 0294200 A2 | 12/1988 |
| EP | 0294200 B1 | 12/1988 |
| EP | 0389272 A2 | 9/1990 |
| EP | 0402872 A1 | 12/1990 |
| EP | 0580385 A1 | 1/1994 |
| EP | 0712638 A1 | 5/1996 |
| EP | 0732116 A2 | 9/1996 |
| EP | 0796631 A2 | 9/1997 |
| EP | 0842672 A2 | 5/1998 |
| EP | 0845276 A2 | 6/1998 |

(56) References Cited

FOREIGN PATENT DOCUMENTS

| | | |
|---|---|---|
| EP | 0865798 A2 | 9/1998 |
| EP | 0922465 A2 | 6/1999 |
| EP | 0935971 A2 | 8/1999 |
| EP | 1119386 B1 | 8/2001 |
| EP | 1125595 A1 | 8/2001 |
| EP | 1 800 706 | 6/2007 |
| EP | 1 938 855 | 7/2008 |
| EP | 2 044 969 | 4/2009 |
| GB | 1529190 A | 10/1978 |
| GB | 2111394 A | 7/1983 |
| GB | 2205499 A | 12/1988 |
| GB | 2 298 580 | 9/1996 |
| GB | 2298580 A * | 9/1996 ............ A61M 16/04 |
| GB | 2298797 A | 9/1996 |
| GB | 2317342 A | 3/1998 |
| GB | 2317830 A | 4/1998 |
| GB | 2318735 A | 5/1998 |
| GB | 2319478 A | 5/1998 |
| GB | 2321854 A | 8/1998 |
| GB | 2323289 A | 9/1998 |
| GB | 2323290 A | 9/1998 |
| GB | 2323291 A | 9/1998 |
| GB | 2323292 A | 9/1998 |
| GB | 2324737 A | 11/1998 |
| GB | 2334215 A | 8/1999 |
| GB | 2359996 A | 9/2001 |
| GB | 2371990 A | 8/2002 |
| GB | 2 404 863 | 2/2005 |
| GB | 2405588 A | 3/2005 |
| GB | 2 444 779 | 6/2008 |
| GB | 2454199 A | 5/2009 |
| GB | 2436294 B | 12/2009 |
| GB | 2 465 453 | 5/2010 |
| JP | 57-110261 | 7/1982 |
| JP | 03039169 A | 2/1991 |
| JP | H07-509154 A | 10/1995 |
| JP | H08-547 A | 1/1996 |
| JP | H09-505211 A | 5/1997 |
| JP | 10118182 A | 5/1998 |
| JP | H10-179745 A | 7/1998 |
| JP | 10216233 A | 8/1998 |
| JP | 10263086 A | 10/1998 |
| JP | 10277156 A | 10/1998 |
| JP | 10314308 A | 12/1998 |
| JP | 10323391 A | 12/1998 |
| JP | 10328303 A | 12/1998 |
| JP | 11128349 A | 5/1999 |
| JP | 11192304 A | 7/1999 |
| JP | 11206885 A | 8/1999 |
| JP | 2000152995 A | 6/2000 |
| JP | 2003-511108 A | 3/2003 |
| JP | 2003528701 A | 9/2003 |
| JP | 2007-514496 A | 6/2007 |
| JP | 2007-533337 A | 11/2007 |
| JP | 2008-136791 A | 6/2008 |
| JP | 2008-526393 A | 7/2008 |
| RU | 2366463 C2 * | 9/2009 ............ A61M 16/04 |
| TW | 200706196 A | 2/2007 |
| TW | 200942206 A | 10/2009 |
| WO | WO9103207 A1 | 3/1991 |
| WO | WO9107201 A1 | 5/1991 |
| WO | WO9112845 A1 | 9/1991 |
| WO | WO9213587 A1 | 8/1992 |
| WO | WO 94/02191 | 2/1994 |
| WO | WO9402191 A1 | 2/1994 |
| WO | WO9533506 A1 | 12/1995 |
| WO | WO9712640 A1 | 4/1997 |
| WO | WO9712641 A1 | 4/1997 |
| WO | WO9816273 A1 | 4/1998 |
| WO | WO9850096 | 11/1998 |
| WO | WO9906093 A1 | 2/1999 |
| WO | WO 99/27840 | 6/1999 |
| WO | WO0009189 A1 | 2/2000 |
| WO | WO 00/20062 | 4/2000 |
| WO | WO0022985 A1 | 4/2000 |
| WO | WO0023135 A1 | 4/2000 |
| WO | WO0061212 A1 | 10/2000 |
| WO | WO0124860 | 4/2001 |
| WO | WO0174431 A2 | 10/2001 |
| WO | WO0232490 A2 | 4/2002 |
| WO | WO 2004/016308 | 2/2004 |
| WO | WO2004030527 A1 | 4/2004 |
| WO | WO 04/089453 | 10/2004 |
| WO | WO 2004/089453 | 10/2004 |
| WO | WO 2005/011784 | 2/2005 |
| WO | WO2005011784 A1 | 2/2005 |
| WO | WO2005023350 A1 | 3/2005 |
| WO | WO 2005/046751 | 5/2005 |
| WO | WO 2005/058402 A1 | 6/2005 |
| WO | WO2006026237 A1 | 3/2006 |
| WO | WO 06/037626 | 4/2006 |
| WO | WO 06/125986 | 11/2006 |
| WO | WO2006125989 A1 | 11/2006 |
| WO | WO2007071429 | 10/2007 |
| WO | WO 07/131267 | 11/2007 |
| WO | WO 2008/001724 | 1/2008 |
| WO | WO 2008001724 A1 * | 1/2008 ............ A61M 16/04 |
| WO | WO 2009/026628 | 3/2009 |
| WO | WO 09/156949 | 12/2009 |
| WO | WO 10/060224 | 6/2010 |
| WO | WO 2010/060227 | 6/2010 |
| WO | WO 2010/066001 | 6/2010 |
| WO | WO2010060226 | 6/2010 |
| WO | WO 2010060226 A1 * | 6/2010 ............ A61M 16/04 |
| WO | WO 2010060227 A1 * | 6/2010 ............ A61M 16/04 |
| WO | WO 10/100419 | 9/2010 |
| WO | WO 13/066195 | 5/2013 |

OTHER PUBLICATIONS

M.O. Abdelatti; "A Cuff Pressure Controller for Tracheal Tubes and Laryngeal Mask Airways" Anaesthesia, 1999, 54, pp. 981-986 (1999 Blackwell Science Ltd).

Jonathan L. Benumo, M.D.; "Laryngeal Mask Airway and the ASA Difficult Airway Algorithm" Medical Intelligence Article; Anesthesiology, V 84, No. 3, Mar. 1996 (686-99).

Jonathan L. Benumo, M.D.; "Management of the Difficult Adult Airway" With Special Emphasis on Awake Tracheal Intubation; Anesthesiology V 75, No. 6: 1087-1110, 1991.

Bernhard, et al.; "Adjustment of Intracuff Pressure to Prevent Aspiration" ; Anesthesiology, vol. 50, No. 4, 363-366, Apr. 1979.

Bernhard, et al.; "Physical Characteristics of and Rates of Nitrous Oxide Diffusion into Tracheal Tube Cuffs" Anesthesiology, vol. 48, No. 6 Jun. 1978, 413-417.

A.I.J. Brain, et al.: "The Laryngeal Mask Airway" Anesthesia, 1985, vol. 40, pp. 356-361.

A.I.J. Brain, et al.: "The Laryngeal Mask Airway—A Possible New Solution to Airway Problems in the Emergency Situation" Archives of Emergency Medicine, 1984, vol. 1, p. 229-232.

A.I.J. Brain; "The Laryngeal Mask—A New Concept in Airway Management" British Journal of Anaesthesia, 1983, vol. 55, p. 801-805.

A.I.J. Brain, et al.: "A New Laryngeal Mask Prototype" Anaesthesia, 1995, vol. 50, pp. 42-48.

A.I.J. Brain; "Three Cases of Difficult Intubation Overcome by the Laryngeal Mask Airway" ; Anaesthesia, 1985, vol. 40, pp. 353-355.

J. Brimacombe; "The Split Laryngeal Mask Airway" ; Royal Perth Hospital, Perth 6001 Western Australia; Correspondence p. 639.

P.M. Brodrick et al.; "The Laryngeal Mask Airway" ; Anaesthesia, 1989, vol. 44, pp. 238-241; The Association of Anaesthetists of Gt Britain and Ireland.

Burgard et al.; "The Effect of Laryngeal Mask Cuff Pressure on Postoperative Sore Throat Incidence" ; Journal of Clinical Anesthesia 8: 198-201, 1996 by Elsevier Science Inc.

Caplan, et al.; "Adverse Respiratory Events in Anesthesia: A Closed Claims Analysis"; Anesthesiology vol. 72, No. 5: 828-833, May 1990.

Donald E. Craven, MD; "Prevention of Hospital-Acquired Pneumonia: Meaning Effect in Ounces, Pounds, and Tons"; Annals of Internal Medicine, vol. 122, No. 3, Feb. 1, 1995, pp. 229-231.

(56) References Cited

OTHER PUBLICATIONS

"Cuff-Pressure-Control CDR 2000"; LogoMed, Klarenplatz 11, D-53578 Windhagen, pp. 1-4.
P.R.F. Davies et al.; "Laryngeal Mask Airway and Tracheal Tube Insertion by Unskilled Personnel"; The Lancet, vol. 336, p. 977-979.
DeMello et al.; "The Use of the Laryngeal Mask Airway in Primary Anaesthesia" Cambridge Military Hospital, Aldershot, Hants GU11 2AN; pp. 793-794.
Doyle et al.; "Intraoperative Awareness: A Continuing Clinical Problem"; Educational Synopses in Anesthesiology and Critical Care Medicine the Online Journal of Anesthesiology vol. 3 No. Jun. 6, 1996, pp. 1-8.
F. Engbers; "Practical Use of 'Diprifusor' Systems"; Anaesthesia, 1998, vol. 53, Supplement 1, pp. 28-34; Blackwell Science Ltd.
Eriksson et al.; "Functional Assessment of the Pharynx at Rest and During Swallowing in Partially Paralyzed Humans" Anesthesiology, vol. 87, No. 5, Nov. 1997, pp. 1035-1042.
J.B. Glen; "The Development of 'Diprifusor': A TCI System for Propofol" Anaesthesia, 1998, vol. 53, Supplement 1, pp. 13-21, Blackwell Science Ltd.
J.M. Gray et al.; "Development of the Technology for 'Diprifusor' TCI Systems"; Anaesthesia, 1998, vol. 53, Supplement 1, pp. 22-27, Blackwell Science Ltd.
M.L. Heath; "Endotracheal Intubation Through the Laryngeal Mask—Helpful When Laryngoscopy is Difficult or Dangerous"; European Journal of Anaesthesiology 1991, Supplement 4, pp. 41-45.
S. Hickey et al.; "Cardiovascular Response to Insertion of Brian's Laryngeal Mask"; Anaesthesia, 1990, vol. 45, pp. 629-633, The Association of Anaesthetists of Gt Britain and Ireland.
Inomata et al.; "Transient Bilateral Vocal Cord Paralysis after Insertion of a Laryngeal Mask Airway"; Anaesthesiology, vol. 82, No. 3, Mar. 1995, pp. 787-788.
L. Jacobson et al.; "A Study of Intracuff Pressure Measurements, Trends and Behaviour in Patients During Prolonged Periods of Tracheal Intubation" British Journal of Anaesthesia (1981), vol. 53, pp. 97-101; Macmillan Publishers Ltd. 1981.
V. Kambic et al.; "Intubation Lesions of the Larynx"; British Journal of Anaesthesia (1978), vol. 50, pp. 587-590; Macmillan Journals Ltd. 1978.
A. Kapila et al.; "Intubating Laryngeal Mask Airway: A Preliminary Assessment of Performance"; British Journal of Anaesthesia 1995, vol. 75: pp. 228-229.
Carl-Eric Lindholm; "Prolonged Endotracheal Intubation" ; Iussu Societatis Anaesthesiologicae Scandinavica Edita Suppllementum XXXIII 1969 v. 33 pp. 29-46.
S. Majumder et al.; "Bilateral Lingual Nerve Injury Following the Use of the Laryngeal Mask Airway" ; Anaesthesia, 1998, vol. 53, pp. 184-186, 1998 Blackwell Science Ltd.
Todd Martin; "Patentability of Methods of Medical Treatment: A Comparative Study"; HeinOnLine—82 J. Pat. & Trademark Off. Soc'y 2000, pp. 381-423.
Merriam-Webster's Collegiate Dictionary Tenth Edition, Springfield, Mass, U.S.A. (Convex) p. 254 & (Saddle) p. 1029.
D.M. Miller; "A Pressure Regulator for the Cuff of a Tracheal Tube" Anaesthesia, 1992, vol. 47, pp. 594-596; 1992 The Association of Anaesthetists of Gt Britain and Ireland.
Muthuswamy et al.; "The Use of Fuzzy Integrals and Bispectral Analysis of the Electroencephalogram to Preddict Movement Under Anesthesia"; Ieee Transactions on Biomedical Engineering, vol. 46, No. 3, Mar. 1999, pp. 291-299.
K. Nagai et al.; "Unilateral Hypoglossal Nerve Paralysis Following the Use of the Laryngeal Mask Airway"; Anaesthesia, 1994, vol. 49, pp. 603-604; 1994 The Association of Anaesthetists of Gt Britain and Ireland.
Lars J. Kangas; "Neurometric Assessment of Adequacy of Intraoperative Anesthetic" Medical Technology Brief, Pacific Northwest National Laboratory, pp. 1-3.
Observations by a third party concerning the European Patent Application No. 99947765.6-2318, dated Jan. 18, 2005.
R.I. Patel et al.; "Tracheal Tube Cuff Pressure"; Anaesthesia, 1984, vol. 39, pp. 862-864; 1984 The Association of Anaesthetists of Gt Britain and Ireland.
Written Opinion of the International Searching Authority for Application No. PCT/GB2006/001913.
Pennant et al.; "Comparison of the Endotracheal Tube and Laryngeal Mask in Airway Management by Paramedical Personnel"; Dept of Anesthesiology, University of Texas Southwestern Medical School; Anesth Analg 1992, vol. 74, pp. 531-534.
Pippin et al.; "Long-Term Tracheal Intubation Practice in the United Kingdom"; Anaesthesia, 1983, vol. 38, pp. 791-795.
J.C. Raeder et al.; "Tracheal Tube Cuff Pressures" Anaesthesia, 1985, vol. 40, pp. 444-447; 1985 The Association of Anaesthetists of Gt Britain and Ireland.
Response to Complaint for matter No. 4b 0 440-05, LMA Deutschland GmbH vs. AMBU (Deutschland) GmbH, dated Feb. 10, 2006.
Rieger et al.; "Intracuff Pressures Do Not Predict Laryngopharyngeal Discomfort after Use of the Laryngeal Mask Airway"; Anesthesiology 1997, vol. 87, pp. 63-67; 1997 American Society of Anesthesiologists, Inc.
R D Seegobin et al.; "Endotracheal Cuff Pressure and Tracheal Mucosal Blood Flow: Endoscopic Study of Effects of Four Large Volume Cuffs"; British Medical Jornal, vol. 288, Mar. 31, 1984, pp. 965-968.
B.A. Willis et al.; "Tracheal Tube Cuff Pressure" Anaesthesia, 1988, vol. 43, pp. 312-314; The Association of Anaesthetists of Gt Britain and Ireland.
L. Worthington et al.; "Performance of Vaporizers in Circle Systems" British Journal of Anaesthesia 1995, vol. 75.
J. Michael Wynn, M.D.; "Tongue Cyanosis after Laryngeal Mask Airway Insertion" Anesthesiology, vol. 80, No. 6, Jun. 1994, p. 1403.
Brimacombe, Joseph R., "Laryngeal Mask Anesthesia" Second Edition, Saunders 2005.
"Anaesthetic and respiratory equipment—Supralaryngeal airways and connectors", International Standard Controlled, ISO 11712, ISO 2009.
Miller, Donald, "A Proposed Classification and Scoring System for Supraglottic Sealing Airways: A Brief Review", Anesth Analg 2004; 99:1553-9.
Benumof, Jonathan, "The Glottic Aperture Seal Airway. A New Ventilatory Device", Anesthesiology, V. 88, No. 5., May 1998, pp. 1219-1226.
McIntyre, John, "History of Anaesthesia" Oropharyngeal and nasopharyngeal airways: I (1880-1995), Can. J. Anaesth 1996, vol. 43, vol. 6, pp. 629-635.
Ishimura, et al., "Impossible Insertion of the Laryngeal Mask Airway and Oropharyngeal Axes", Anesthesiology, V. 83, No. 4., Oct 1995, pp. 867-869.
Verghese, et al., "Clinical assessment of the single use laryngeal mask airway—the LMA-Unique", British Journal of Anaesthesia 1998; vol. 80: 677-679.

\* cited by examiner

LARYNGEAL MASK FOR USE WITH AN ENDOSCOPE

This application is the U.S. National Phase under 35 U.S.C. § 371 of International Application No. PCT/GB2012/000876, filed Nov. 29, 2012, which claims priority to Great Britain Patent Application No. 1120628.1, filed Nov. 30, 2011.

The present invention relates to an endoscopy device, and more particularly to an endoscopy device that also provides an airway.

Certain surgical and diagnostic endoscopy procedures require the insertion of instruments or viewing devices into the upper gastrointestinal tract of a patient. For example, in endoscopy an endoscope is passed directly through the mouth of the patient, into the oesophagus and down to the stomach and duodenum. The endoscope includes at its tip a light and a visualisation device such as a camera and can include a working channel down which the operator can pass other instruments. In an endoscopy the patient is usually given some form of local anesthetic, and in some cases also a sedative. A mouth guard is placed between the patient's teeth and the endoscope is passed through it, at which point the patient is required to swallow the leading or distal end of the endoscope. Once the patient has swallowed the distal end, the operator must then push the endoscope by manual force down through the oesophagus into the stomach and duodenum.

A number of problems can be experienced with procedures such as endoscopy that require insertion of instruments or viewing devices blind and under manual force into a patient's oesophagus. Firstly, the use of local anaesthetics and sedatives is undesirable in some patients and may cause cardio respiratory complications, including small variations in a patient's vital signs to arrhythmias, respiratory arrest, myocardial infarction, shock and possibly even death (page 7, Complications of Upper Gastrointestinal Endoscopy, Riley and Alderson, BSG Guidelines in Gastroenterology, November 2006). In addition, upper gastrointestinal endoscopy may cause problems such as infection, perforation or in some cases, bleeding. Specifically, perforation may take place in the pharynx or oesophagus of a patient, often at sites of pathology or as a result of blind insertion of an endoscope (pages 7 and 8, Complications of Upper Gastrointestinal Endoscopy, Riley and Alderson, BSG Guidelines in Gastroenterology, November 2006). Furthermore, it is known that therapeutic upper gastrointestinal endoscopy often takes a longer amount of time than diagnostic endoscopy. In addition, in many cases the use of such a technique may be more uncomfortable for the patient concerned and may require a greater level of intravenous sedation, which combined with intravenous analgesia, may cause cardio respiratory complications (page 8, Complications of Upper Gastrointestinal Endoscopy, Riley and Alderson, BSG Guidelines in Gastroenterology, November 2006).

In addition, following upper gastrointestinal endoscopy, patients may experience some minor discomfort to the throat and abdomen. Although these complaints are generally considered to be minor, one prospective study has found that approximately 2% of patients went on to seek medical advice, with some patients being hospitalised (page 7, Complications of Upper Gastrointestinal Endoscopy, Riley and Alderson, BSG Guidelines in Gastroenterology, November 2006).

At present, an endoscope is usually inserted into the oesophagus of a patient on its own, i.e. in the absence of a guide device. This typically causes problems during general anaesthesia as it may interfere with and obstruct the breathing of the patient, due to the fact that little or no air supply is provided. Therefore, in such situations, it is important to carry out the investigative procedure quickly, minimising the amount of time in which the endoscope is inserted. This may result in less information being obtained during the investigative procedure, may be dangerous to the patient and may result in increased costs being incurred.

It is known to use a guide tube to provide a path for travel of an endoscope into a body cavity. EP 2368481 and EP 2368483 relate to a guide device for guiding the entry of an endoscope into a body cavity of a patient.

Artificial airway devices such as the laryngeal mask airway device are well known devices useful for establishing airways in unconscious patients. In its most basic form a laryngeal mask airway device consists of an airway tube and a mask carried at one end of the airway tube, the mask having a peripheral formation often known as a "cuff" which is capable of conforming to and of fitting within, the actual and potential space behind the larynx of the patient so as to form a seal around the laryngeal inlet. The cuff can be inflatable, and in most variants it surrounds a hollow interior space or lumen of the mask, the at least one airway tube opening into the lumen. U.S. Pat. No. 4,509,514 is one of the many publications that describe laryngeal mask airway devices such as this. It is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulation of the patient's head, neck and jaw. Further, the laryngeal mask airway device provides ventilation of the patient's lungs without requiring contact with the sensitive inner lining of the trachea and the size of the airway established is typically significantly larger than the size of the airway established with an endotracheal tube. Also, the laryngeal mask airway device does not interfere with coughing to the same extent as endotracheal tubes. Largely due to these advantages, the laryngeal mask airway device has enjoyed increasing popularity in recent years.

During endoscopy, it is preferable for an endoscope to be thin and flexible, in order to assist in examination of the upper gastrointestinal tract of a patient. Such a device would generally not be suitable for use with a laryngeal mask which would typically restrict the movement of the endoscope within the patient. In addition, the provision of a laryngeal mask in combination with an endoscope may present difficulties to a user as the endoscope may interfere with insertion of the laryngeal mask within the oesophagus of a patient, such that the insertion of the laryngeal mask in combination with an endoscope would typically be more difficult when compared with insertion of the mask alone.

It is an object of the present invention to seek to mitigate problems such as these.

According to a first aspect of the invention there is provided an endoscopy device for facilitating the use of a endoscope, comprising at least one airway tube and a mask carried at one end of the at least one airway tube, the mask having a distal end and a proximal end and a peripheral formation capable of conforming to, and of fitting within, the actual and potential space behind the larynx of the patient so as to form a seal around the circumference of the laryngeal inlet, the peripheral formation surrounding a hollow interior space or lumen of the mask and the at least one airway tube opening into the lumen of the mask, the device further comprising a conduit adapted for passage of an endoscope into the oesophagus of a patient when the mask is in place.

The provision of an endoscopy device in accordance with the present invention has the combined benefits of establishing an airway within a patient and protecting the airway from regurgitation or vomiting that might be caused by endoscopy. Thus, the device of the present invention advantageously assists in the safe and accurate insertion of an endoscope within the oesophagus of a patient, whilst at the same time establishing an airway within the patient.

Preferably, the device of the present invention comprises a proximal end and a distal end, wherein a major axis (20 of FIG. 2) is provided therebetween, and wherein a conduit (8 of FIG. 2) is provided at an angle β (21 of FIG. 2) such that it is offset to the midline with respect to the major axis of the device. Advantageously, the provision of the conduit at an angle β which is offset to the midline enables both the conduit and the airway tube to be accommodated within the oesophagus of a patient, increasing the amount of space available for the airway tube within the oesophagus and preventing obstruction of the airway. Typically, the cuff and airway tube are positioned substantially adjacent to the midline with respect to the major axis of the device.

Typically, the device of the present invention minimises the frictional contact between the inside walls of the conduit and an endoscope inserted therein. Advantageously, the device of the present invention assists in the insertion of an endoscope within the conduit and thus the oesophagus of a patient.

Preferably, the conduit has a large bore diameter. Typically, the conduit has a diameter of between about 5 and 25 mm, more typically between about 10 and 20 mm and most typically about 15 mm, depending on the size of the endoscopy device. Advantageously, the diameter of the conduit allows the passage of an endoscope through the conduit. Thus, the conduit forms an "operating channel" through which a surgeon can view the upper gastrointestinal tract of a patient. In addition, the diameter of the conduit may be varied depending on the anatomy of a patient. Preferably, the radial wall thickness of the conduit is between about 1 to 2 mm.

Preferably, the conduit comprises a plurality of bores. Typically, the conduit comprises a plurality of channels, advantageously providing a structure having an increased rigidity. In addition, the conduit is preferably substantially flexible to assist in the insertion of the device within the anatomy of the patient.

In a preferred embodiment, the conduit comprises a silicone material. In another embodiment, the conduit may comprise a plastics material, such as polyvinylchloride (PVC), or rubber. Preferably, the conduit has a durometer hardness of between 60 and 70 Shore. This durometer hardness has the advantage that, upon insertion, less force is required to insert the conduit within the oesophagus of the patient.

Typically, the endoscopy device in accordance with the present invention is inserted into the upper oesophageal sphincter of a patient. Due to the narrow dimensions of this region of the anatomy, careful insertion of the device is required. Typically, the endoscopy device in accordance with the present invention is inserted into the upper oesophageal sphincter by means of the tip of the cuff, which provides guided insertion of the device. Furthermore, the distal flexibility of the tip of the device may assist in tracking the posterior curvature of the throat of a patient upon insertion of the device and reduces trauma to the throat of the patient.

The use of an endoscopy device in accordance with the present invention in combination with an endoscope is safer than use of the endoscope alone and advantageously allows the endoscope to be inserted within the oesophagus of a patient for a longer period of time.

Typically, the peripheral formation may be inflatable. Preferably, the peripheral formation is an inflatable cuff. The cuff is typically capable of conforming to and fitting within the actual and potential space behind the larynx of the patient so as to form a seal around the laryngeal inlet. Typically, the cuff extends from a proximal end to a distal end. It is preferred that the mask describes a substantially convex curve, from a proximal to distal end. It is further preferred that the mask comprises a backplate, the backplate having a dorsal side and a ventral side, the dorsal side being substantially smooth and having a convex curvature across its width. It is also preferred that the dorsal surface of the airway tube corresponds in curvature to the curvature across the width of the backplate. All of these expedients assist in making insertion of the mask easier.

The airway tube preferably comprises a material that is relatively more rigid than the material of the mask body. Typically, the airway tube has a smaller diameter than the diameter of the conduit, thus providing more space for the conduit upon insertion of the device within a patient. Preferably, the airway tube is reinforced such that the formation of kinks within the tube is avoided. Both the airway tube and the mask body preferably comprise a plastics material. In one embodiment, the airway tube may comprise a silicone material.

In some embodiments, the airway tube may comprise a connector element at the proximal end thereof. The connector element may be provided to connect the airway tube to a gas supply. In a preferred embodiment, the airway tube does not comprise a connector element at the proximal end thereof. Advantageously, the absence of a connector element at the proximal end of the airway tube assists in the insertion of the airway tube within the oesophagus of a patient.

In a preferred embodiment, the conduit has a length such that, in use, it extends from the distal end of the mask, passes through the mouth of a patient and emerges between the teeth of the patient. Advantageously, the conduit and thus the endoscope may be inserted through the mouth of a patient.

In one embodiment, the airway tube includes a relatively softer wall portion adjacent a point that, in use, will be adjacent the patient's teeth. It is preferred that the relatively softer portion forms a part of a bite block. The provision of a bite block at a relatively softer portion of the airway tube has the advantage that it guards against damage to the teeth of a patient by virtue of the less rigid parts. In another embodiment, a bite block may be provided on the conduit. The provision of a bite block on the airway tube or conduit has the additional advantage that it prevents collapse of the channel provided by either component. For the avoidance of doubt, the endoscopy device may or may not have means for removal of oesophageal material.

Preferably, the distal end of the conduit is substantially adjacent to the distal end of the cuff. More preferably, the distal end of the conduit is provided at an angle α to the horizontal plane (wherein the horizontal plane is perpendicular to the major axis of the device when the device is in a substantially linear conformation). Typically, the angle α is about 10 to 15 degrees to the horizontal plane, and more preferably about 45 degrees to the horizontal plane. Preferably, the angle α is an acute angle. The provision of a conduit having a distal end which is provided at an angle α with respect to the horizontal plane assists in the insertion of the device within a patient. Advantageously, the greater the size of the angle α with respect to the horizontal plane, the easier the insertion of the device within a patient. Preferably, the distal end of the conduit does not extend significantly beyond the distal end the cuff, such that it does not interfere with the guiding means provided by the tip of the cuff (at the distal end of the cuff) during insertion of the device.

Typically, the conduit may be positioned such that it projects in a left or right direction with respect to the major axis of the device, when viewed from the front of the device. Advantageously, the direction in which the conduit projects relative to the major axis of the device may be selected depending on whether the person operating the endoscopy device is left or right handed.

In a preferred embodiment, an aperture may be provided within the cuff. More preferably, an aperture may be provided at the distal end of the cuff. Advantageously, the provision of an aperture within the cuff facilitates the attachment of the conduit to the cuff. In addition, the provision of an aperture within the cuff may assist in the use of an endoscope to view the upper gastrointestinal tract of a patient, when such an instrument is inserted within the conduit.

Typically, the conduit adopts a straight or linear configuration. In another embodiment, the conduit may be moulded such that it is curved and follows the anatomical shape of a patient's airway.

In a preferred embodiment, the endoscopy device comprises a conduit and an airway tube that are maintained in a configuration such that they are separate from one another. This is advantageous, as it allows an airway to be established upon insertion of the device and ensures that the airway is protected from regurgitation and/or vomiting that may occur as a result of insertion of the endoscope. In another embodiment, the airway tube and conduit may be connected to one another. In this embodiment, it would also be necessary for the components to separate from one another at a region of the device, in order to establish an airway on insertion of the device and protect the airway from regurgitation and/or vomiting that may occur as a result of insertion of the endoscope.

The invention will further be described by way of example and with reference to the following drawings, in which, FIG. 1 is front perspective view of a portion of a device according to the present invention;

Figure 1:
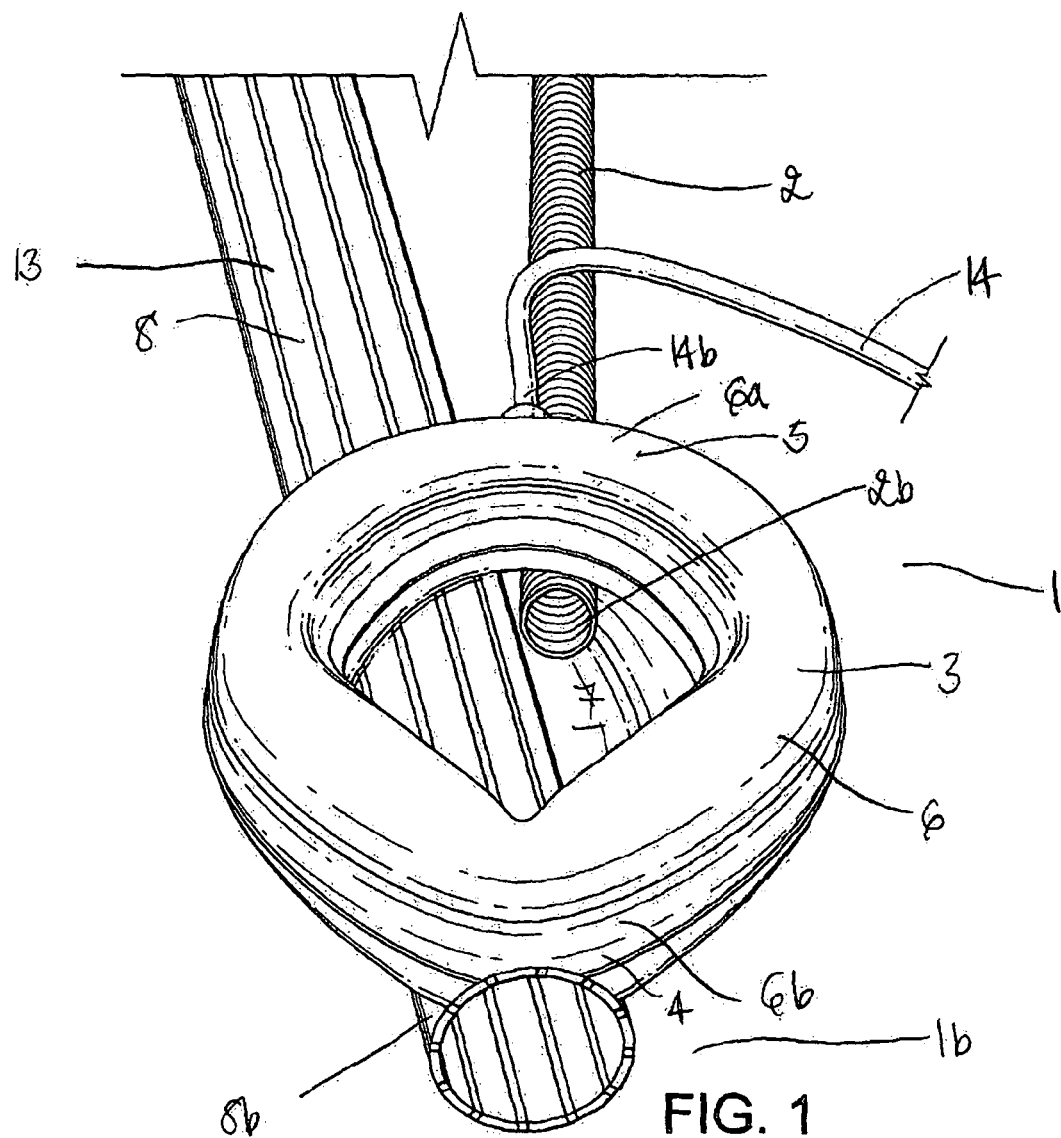

Referring now to the drawings, there is illustrated a device 1 for facilitating the use of a gastroscope, comprising at least one airway tube 2 and a mask 3 carried at one end of the at least one airway tube, the mask 3 having a distal end 4 and a proximal end 5 and a peripheral formation 6 capable of conforming to, and of fitting within, the actual and potential space behind the larynx of the patient so as to form a seal around the circumference of the laryngeal inlet, the peripheral formation 6 surrounding a hollow interior space or lumen 7 of the mask 3 and the at least one airway tube 2 opening into the lumen 7 of the mask, the device further comprising a conduit 8 adapted for passage of a gastroscope into the oesophagus of a patient when the mask 3 is in place.

In terms of the overall appearance, the device 1 in accordance with the present invention is somewhat similar to prior art laryngeal mask airway devices, in that it consists of the basic parts which make up most, if not all, such devices, i.e. an airway tube 2 and a mask portion 3. With reference to the Figures, the device 1 has a proximal end 1a (the end nearest the user when the device is in use), a distal end 1b (the end farthest from the user when the device is in use), a dorsal or pharyngeal side, a ventral or laryngeal side, and right and left sides.

The airway tube 2, extends from a proximal end 2a to a distal end 2b, and the distal end 2b opens into the interior of the hollow mask portion 3. The airway tube 2 may be resiliently deformable or relatively rigid, to enable it to assist in insertion of the device 1 into a patient, acting as a handle and a guide. The airway tube 2 may be made of any material that is currently used for such purposes as will be apparent to one of skill in the art, for example, silicone rubber or plastics materials. It may be straight and flexible or moulded into an appropriately anatomically-curved shape.

Referring firstly to the embodiment of FIGS. 1 to 7, the mask portion 3 includes a body part often referred to as a backplate 9 (see FIG. 3) and a peripheral formation which may take the form of an inflatable cuff 6, the inflatable cuff 6 extending from a proximal end 6a to a distal end 6b. The inflatable cuff 6 may be provided with an inflation line 14. The inflatable cuff 6 is advantageously capable of conforming to and fitting within the space behind the larynx to form a seal around the circumference of the laryngeal inlet without the device 1 penetrating into the interior of the larynx. Different sizes of mask are needed for different sizes of patient.

The cuff 6 may comprise blow moulded PVC and may take the form of a generally elliptical inflatable ring. The cuff 6 is typically integrally formed in one piece.

It is preferred that the mask describes a substantially convex curve, from the proximal to distal end. It is further preferred that the backplate 9 comprises a dorsal side and a ventral side, the dorsal side being substantially smooth and having a convex curvature across its width. It is also preferred that the dorsal surface of the airway tube 2 corresponds in curvature to the curvature across the width of the backplate 9. The backplate 9 is typically formed by moulding from a Shore 50A Vythene PVC+PU. This material is typically substantially softer and more deformable than the material of airway tube 2. The backplate 9 typically comprises a generally oval moulding when viewed from the dorsal or ventral directions.

In contrast to prior art laryngeal mask airway devices, the device 1 according to the invention includes a conduit 8, which conduit 8 is provided to facilitate insertion of a gastroscope, such as a fibrescope or an endoscope, into the oesophagus of a patient when the mask 3 is in place. In this embodiment the device 1 of the present invention comprises a proximal end 1a and a distal end 1b, wherein a major axis is provided therebetween, and wherein the conduit 8 may be provided at an angle such that it is offset to the midline with respect to the major axis of the device. This is of benefit as in some cases there may not be enough space to comfortably accommodate the conduit 8 and the airway tube 2 if they were both provided within the same plane. Thus, the provision of the conduit 8 at an angle offset to the midline with respect to the major axis of the device has the advantage that it allows both the conduit 8 and the airway tube 2 to be more comfortably accommodated within the oesophagus of a patient. In addition, in this embodiment, the conduit 8 does not obstruct the airway tube and thus the airway established by the device.

Figure 4:
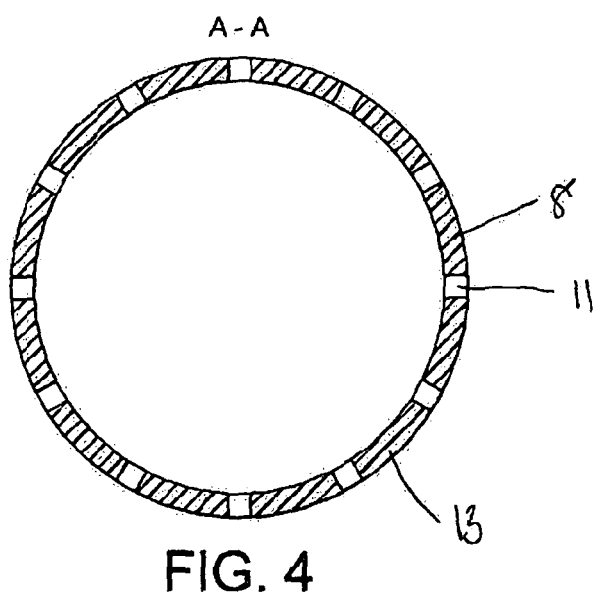
FIG. 4 is cross section view of the conduit of the device of in accordance with the present invention.
Figure 5:
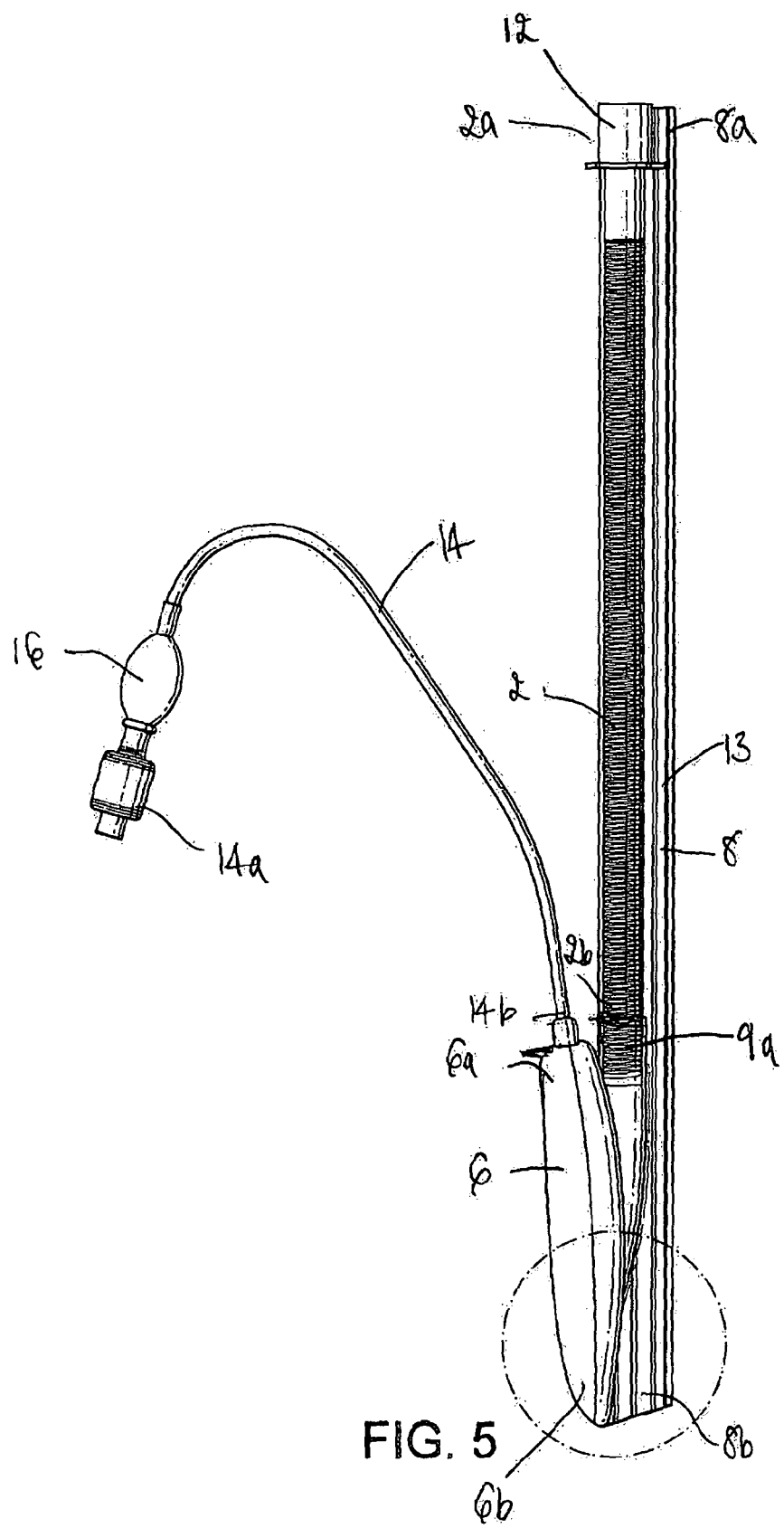
FIG. 5 is a side view of the device in accordance with the present invention, when viewed in the direction of the airway tube.

The conduit 8 preferably has a relatively large bore diameter. Typically, the conduit has a diameter of between 5 and 25 mm, more typically between 10 and 20 mm and most typically about 15 mm. Such a diameter may be provided to allow the passage of a gastroscope such as an endoscope or fibrescope through the conduit 8. However, the diameter of the conduit 8 may be varied depending on the anatomy of a patient. Preferably, the conduit 8 comprises a plurality of bores 11 (as shown in FIG. 4) which add flexibility. Preferably, the conduit 8 comprises a plurality of channels or webs 13 between the bores 11, which channels 13 confer an increased rigidity to the conduit 8. Advantageously, the conduit 8 also maintains a degree of flexibility, thus assisting in the insertion of the device within the oesophagus of a patient. In addition, the device 1 of the present invention minimises the frictional contact between the inside walls of the conduit 8 and a gastroscope inserted therein, thus assisting in the insertion of a gastroscope within the conduit 8, and thus within the oesophagus of a patient.

Figure 6:
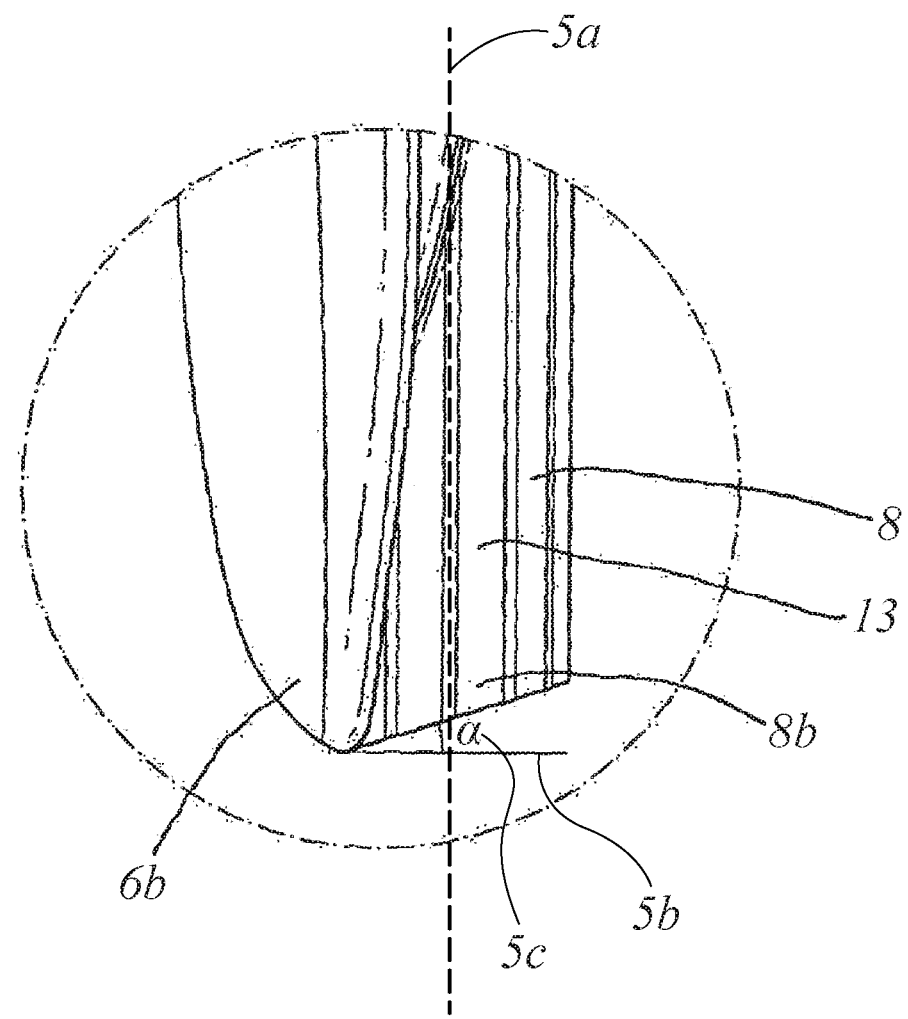
FIG. 6 is an side view of the end of the device of FIG. 5, showing the angle α to which the conduit is positioned relative to the horizontal plane.
Figure 7:
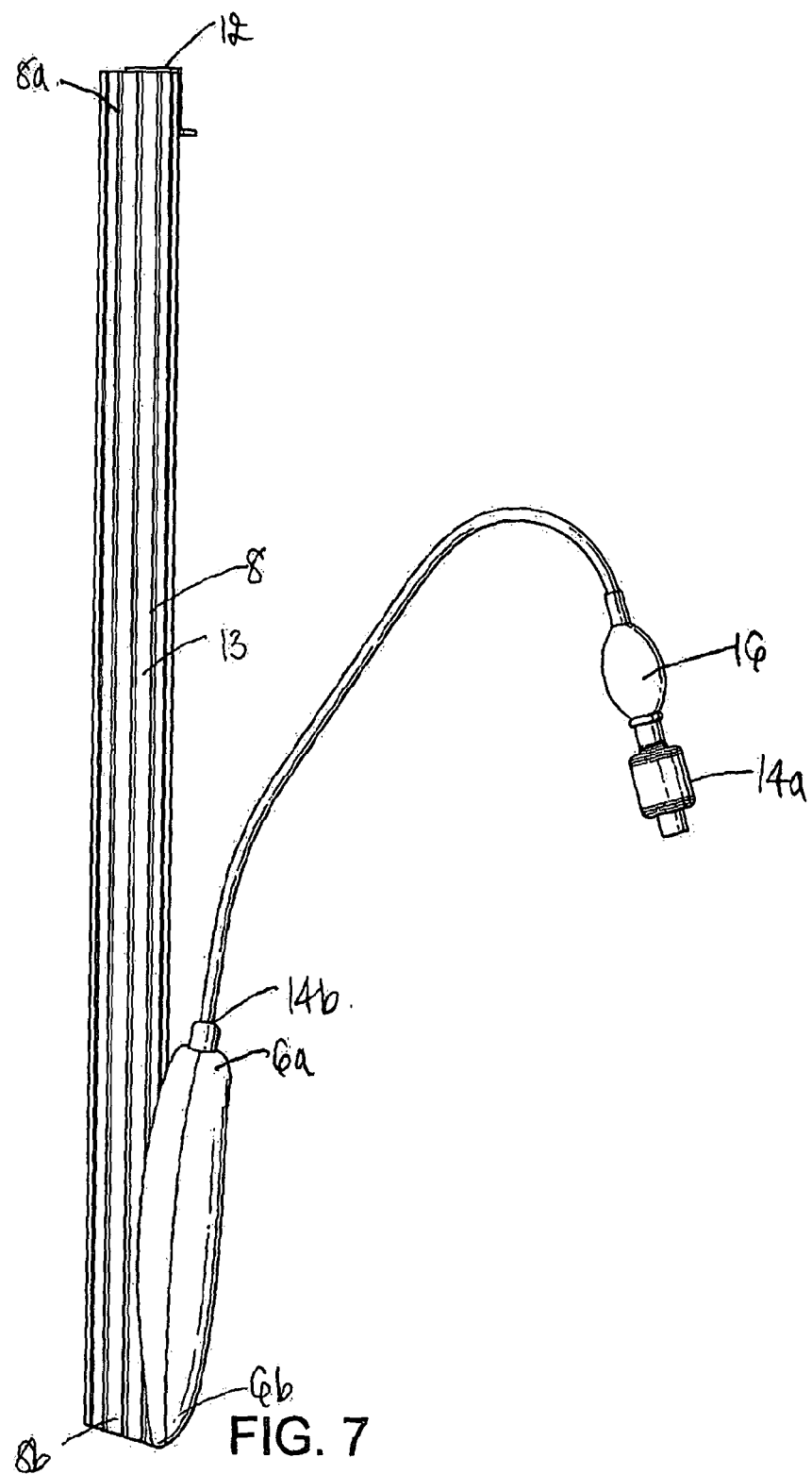
FIG. 7 is a side view of the device of the present invention, when viewed in the direction of the conduit.

The conduit 8 preferably extends through the mask portion 3 of the device and contacts the distal end 6b of the cuff 6. Preferably, the distal end 8b of the conduit 8 is provided adjacent to the distal end 6b of the cuff 6. Preferably, the distal end 8b of the conduit 8 is provided at an angle α (5c) to the horizontal plane 5b (wherein the horizontal plane is substantially perpendicular to the major axis 5a of the device 1 when the device is in a substantially linear conformation). Preferably, the angle α is about 10 to 15 degrees to the horizontal plane, and more preferably at about 45 degrees to the horizontal plane. The provision of the conduit 8 having a distal end 8b which is provided at an angle α to the horizontal plane assists in the insertion of the device 1 within the oesophagus of a patient. Preferably, the distal end 8b of the conduit 8 does not extend significantly beyond the distal end of the cuff 6 (i.e. at the tip of the cuff), such that it does not interfere with the guiding means provided by the tip of the cuff 6 during insertion of the device 1. This can be seen in FIGS. 5 and 6, wherein FIG. 6 illustrates the region within the circle shown in FIG. 5. Specifically, with reference to FIG. 6, the distal end 8b of the conduit 8 is provided at an angle α (5c) to the horizontal plane 5b. Typically, as the angle of a is increased with respect to the horizontal plane 5b, the device 1 becomes easier to insert and causes less trauma to the oesophagus of a patient during insertion thereof.

Throughout most of its length, the conduit 8 may conveniently be moulded or extruded from a flexible or elastomeric material such as silicone or other plastic or rubber, preferably of a durometer hardness in the range 60 to 70 Shore. For use in adult humans, the inner diameter (i.d.) of the conduit 8 may be about 15 mm, and the radial wall thickness may be about 1 to 2 mm.

Figure 2:
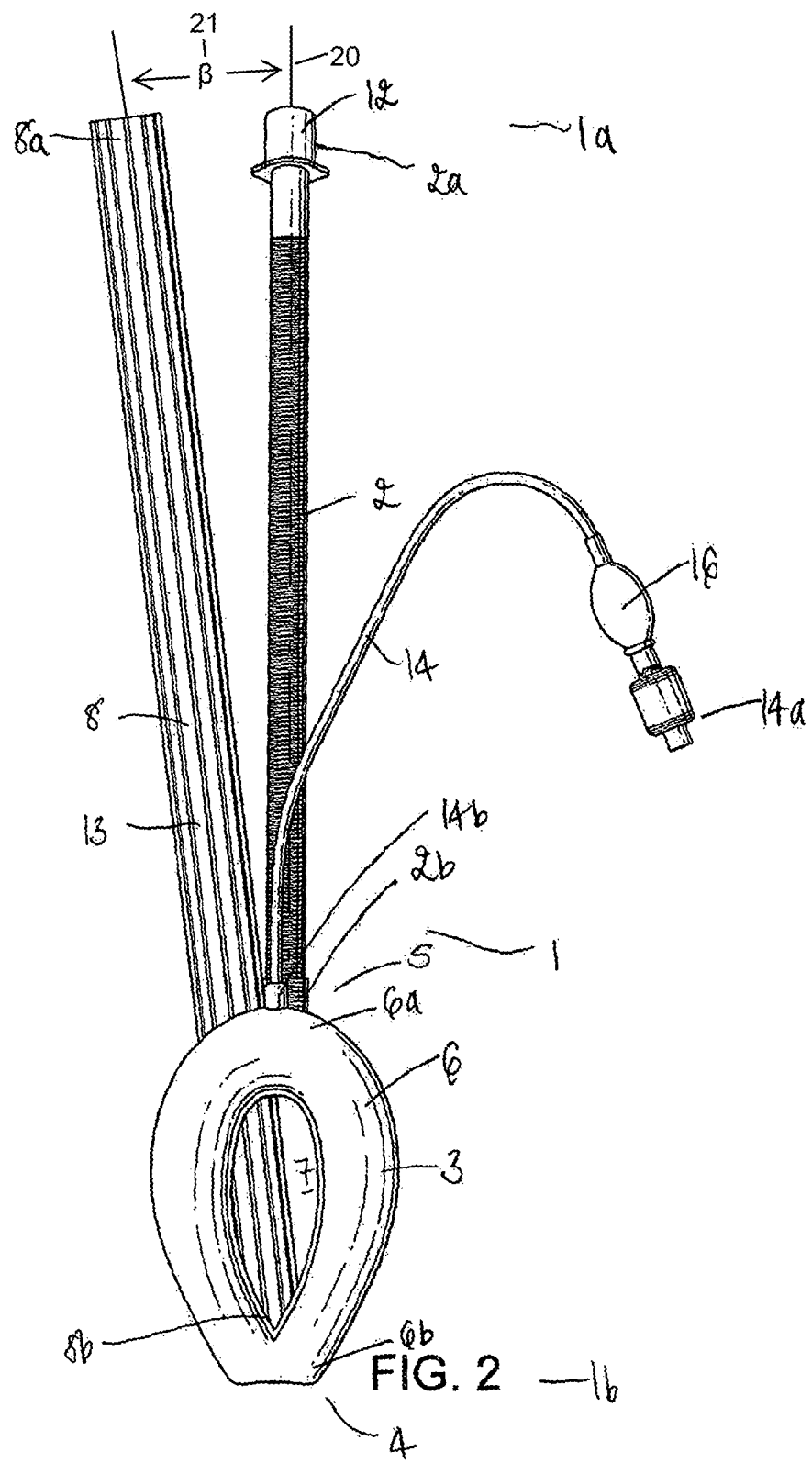
FIG. 2 is an underplan view of the device in accordance with the present invention.
Figure 3:
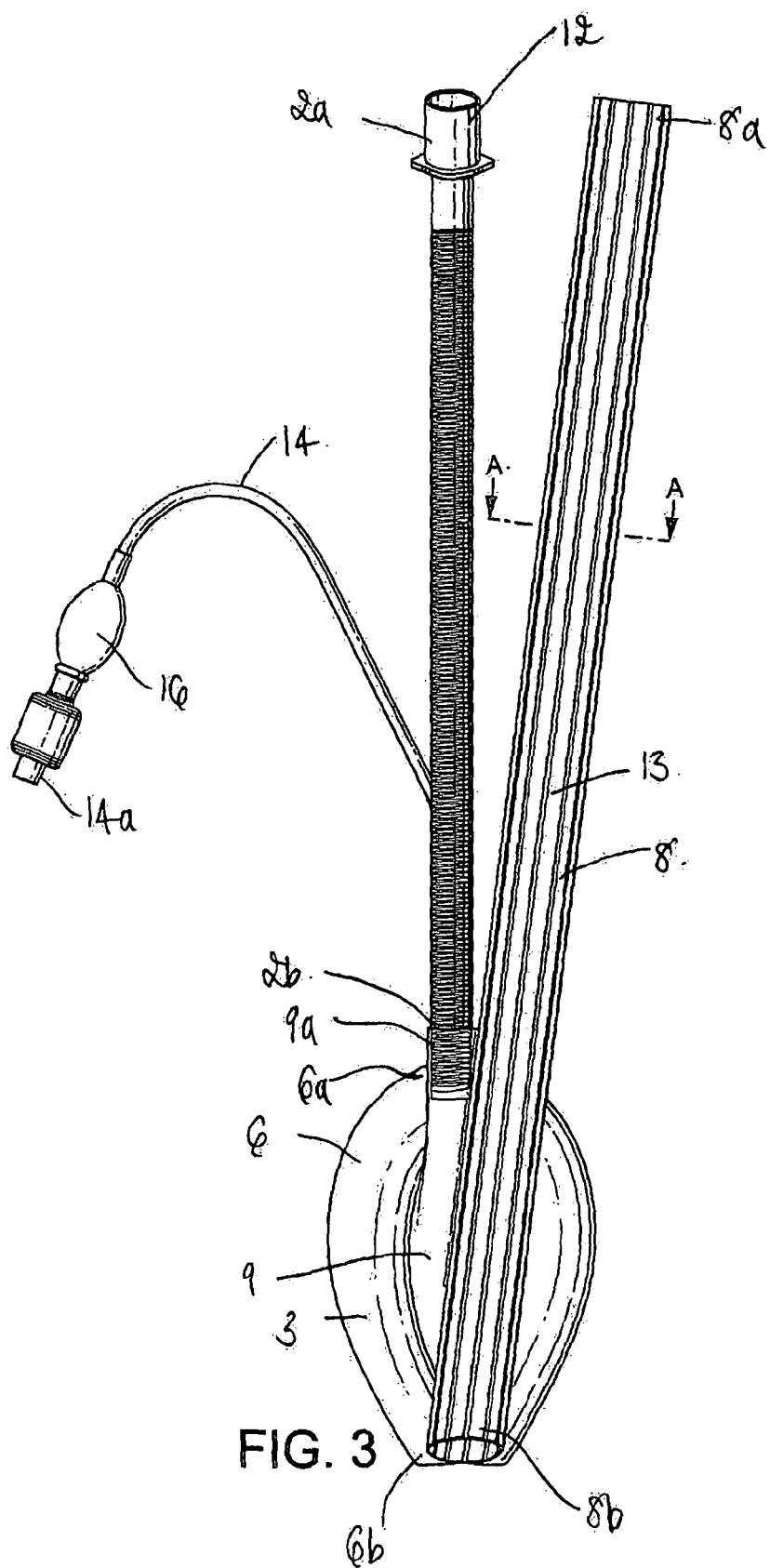
FIG. 3 is a plan view of the device in accordance with the present invention.

FIG. 2 shows a device in accordance with one embodiment of the present invention, wherein a connector 12 is provided at the proximal end 2a of the airway tube 2. In this embodiment, the connector 12 allows for connection of the airway tube 2 to a gas supply. The connector 12 is formed from a relatively rigid plastics material (when compared with the airway tube 2), to enable ease of connection of air lines and suction. However, in a preferred embodiment, the device does not comprise a connector at the proximal end 2a of the airway tube 2. In the embodiment wherein a connector is not provided at the proximal end 2a of the airway tube 2, the insertion of the device 1 within the oesophagus of the patient is improved.

As shown in FIG. 2, the device 1 also preferably includes an inflation line 14 for selectively inflating and deflating the inflatable cuff 6, which inflation line 14 extends from a distal end 14b that is coupled to the proximal end 6a of cuff 6 to a proximal end 14a that is located outside of the patient when the device 1 is in use. A check valve 16 is typically located within the flexible tube 14.

In use, the device 1 is inserted through a patient's mouth and down through the throat past the epiglottis until the mask 3 comes to rest with the distal end of the cuff 6b in the base of the throat, lying against the upper end of the normally closed oesophagus (which the mask 3 cannot easily enter because of its dimensions). The cuff 6 is then inflated to seal around the inlet to the larynx.

After insertion of the device, a gastroscope such as a fibrescope or an endoscope may be inserted through the conduit 8. The provision of the conduit 8 at an angle, such that it is offset to the midline with respect to the major axis of the device 1, has the advantage that it does not obstruct the airway tube 2 and provides more space for the conduit 8 and the airway tube 2 within the oesophagus of the patient. Thus, an airway is established within a patient by means of the airway tube 2 and a gastroscope may simultaneously be inserted through the conduit 8.

Figure 8:
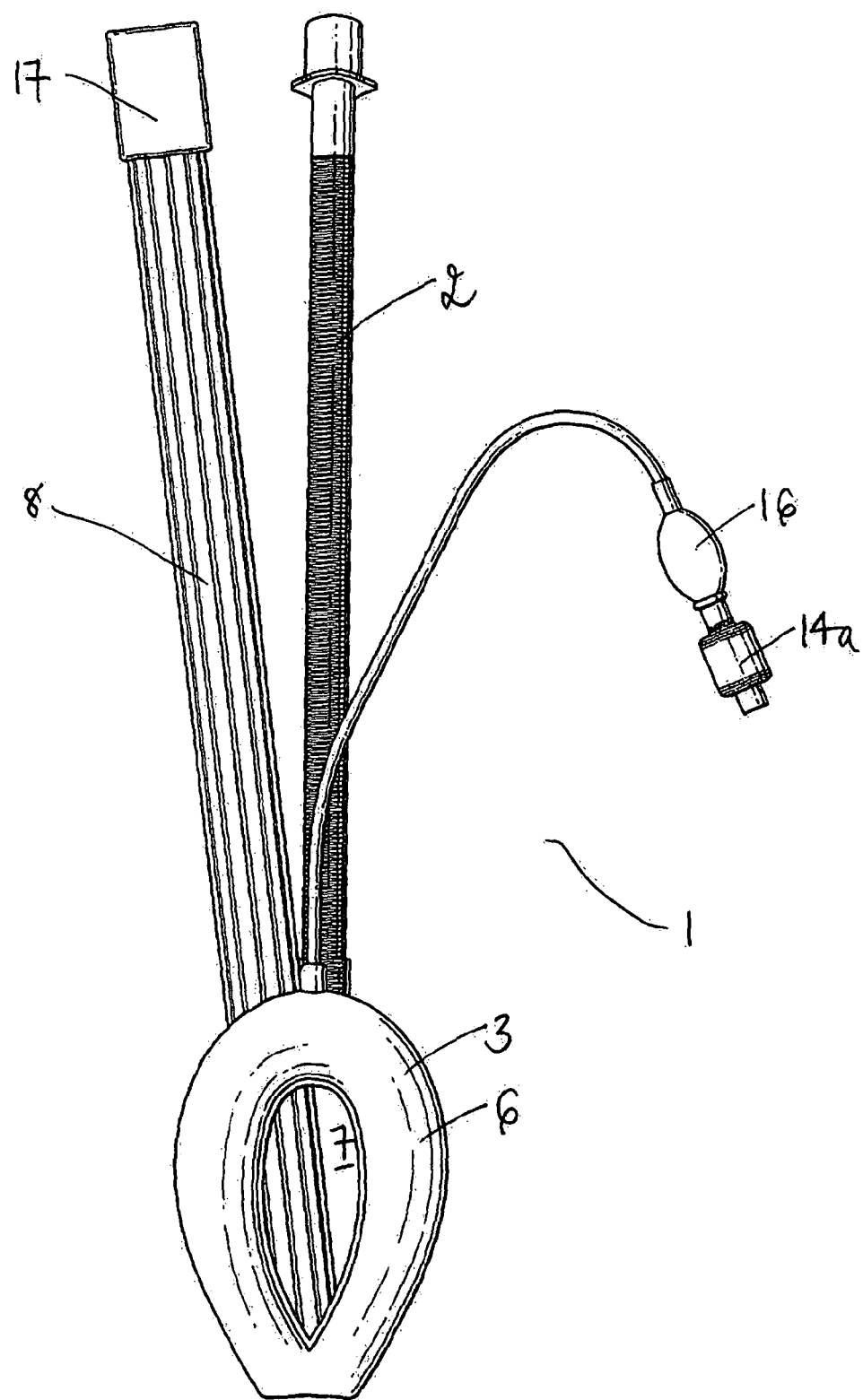
FIG. 8 is an underplan view of a second embodiment of device according to the invention.
Figure 9:
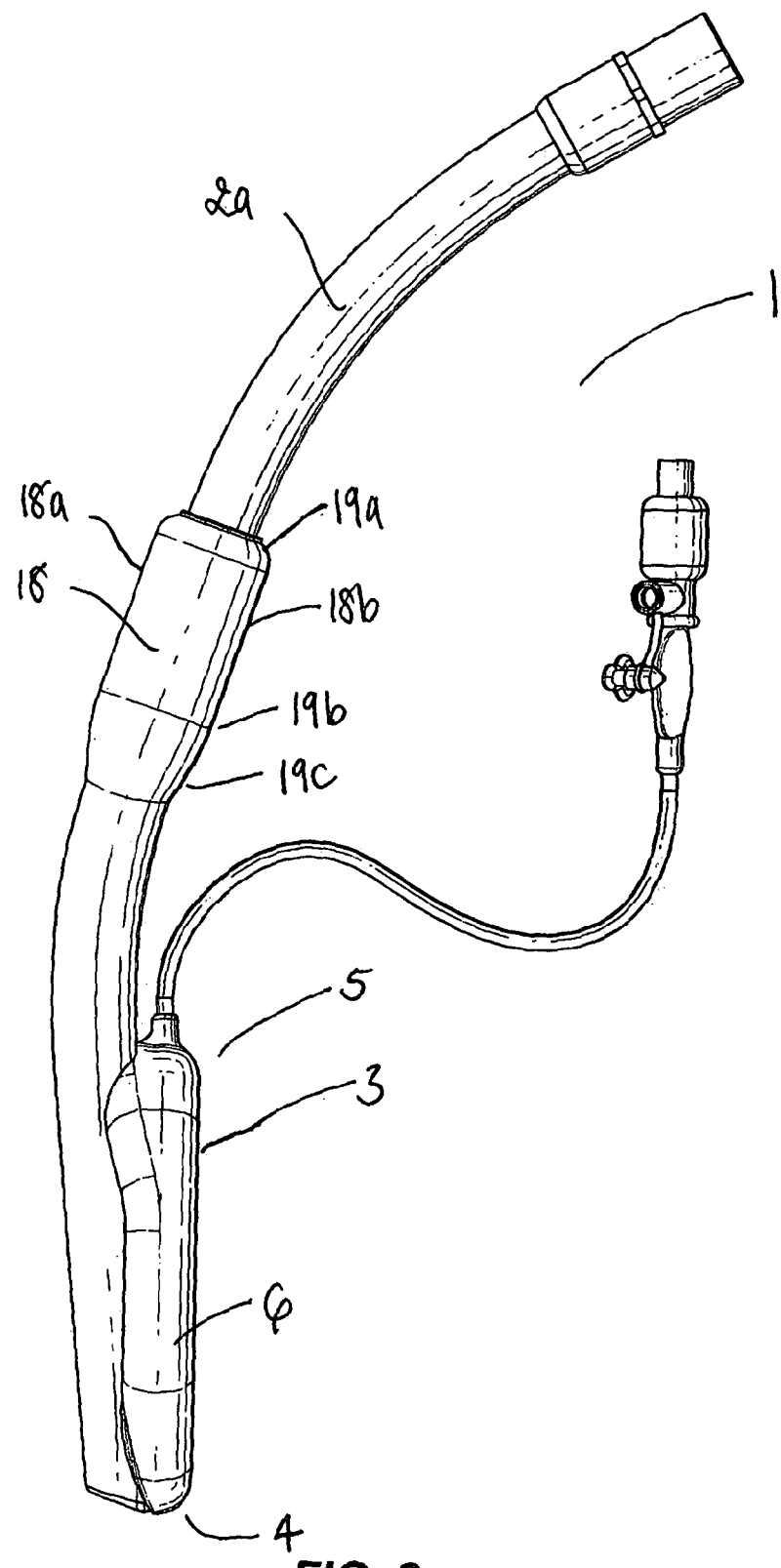
FIG. 9 is a side view of a third embodiment of device according to the invention.
Figure 10:
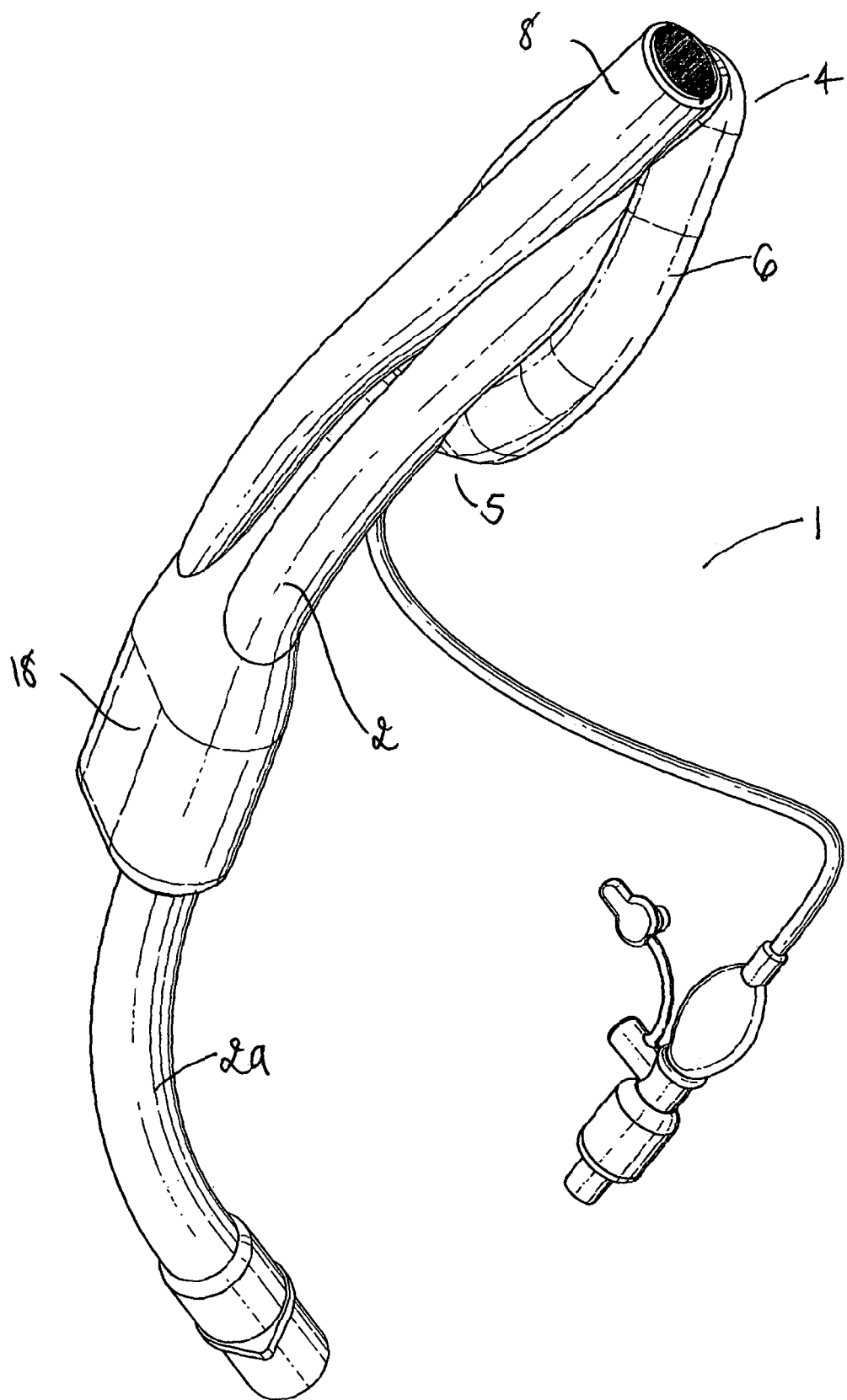
FIG. 10 is a front perspective view of the device of FIG. 9 viewed from the left.
Figure 11:
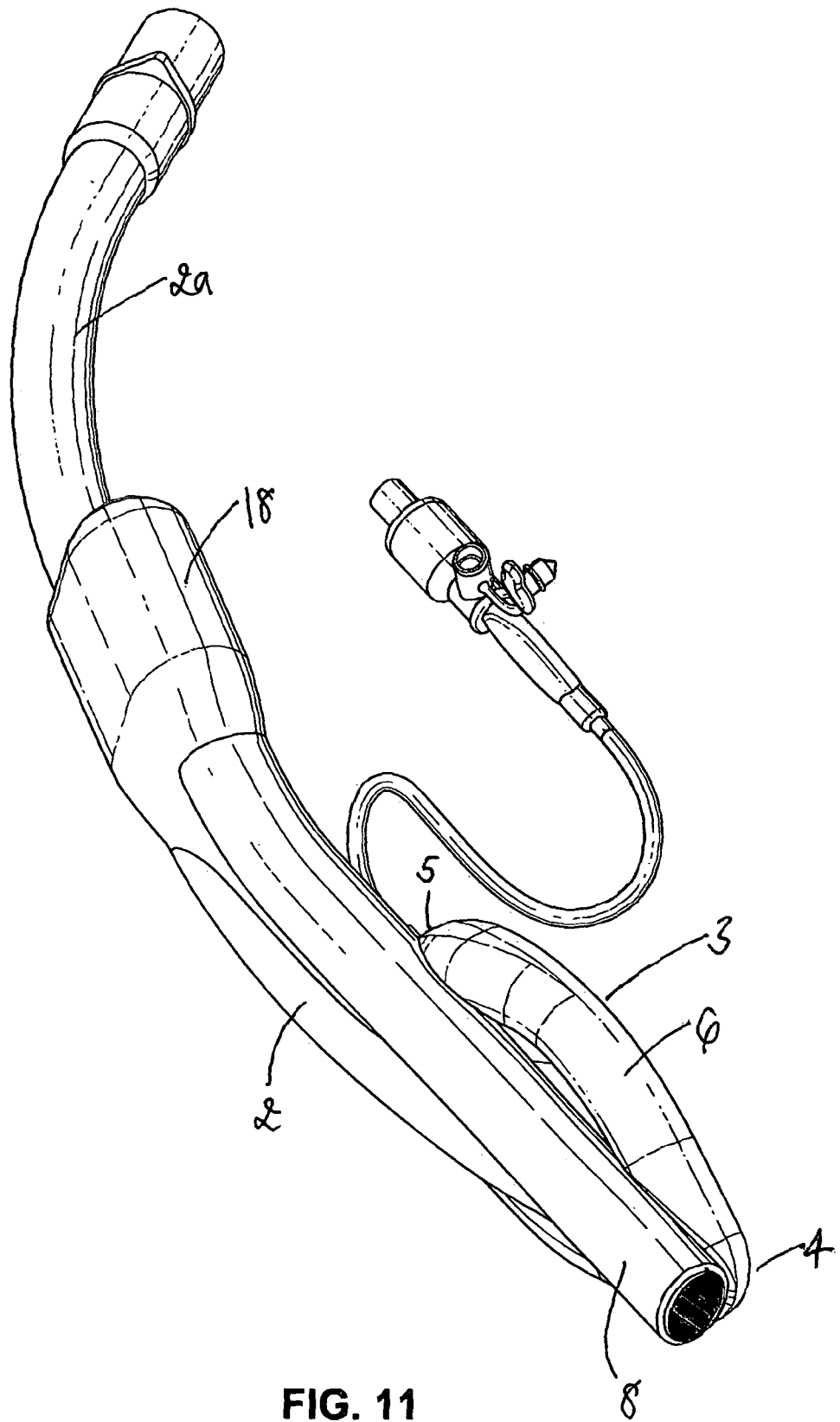
FIG. 11 is a front perspective view of the device of FIG. 9 viewed from the right.
Figure 12:
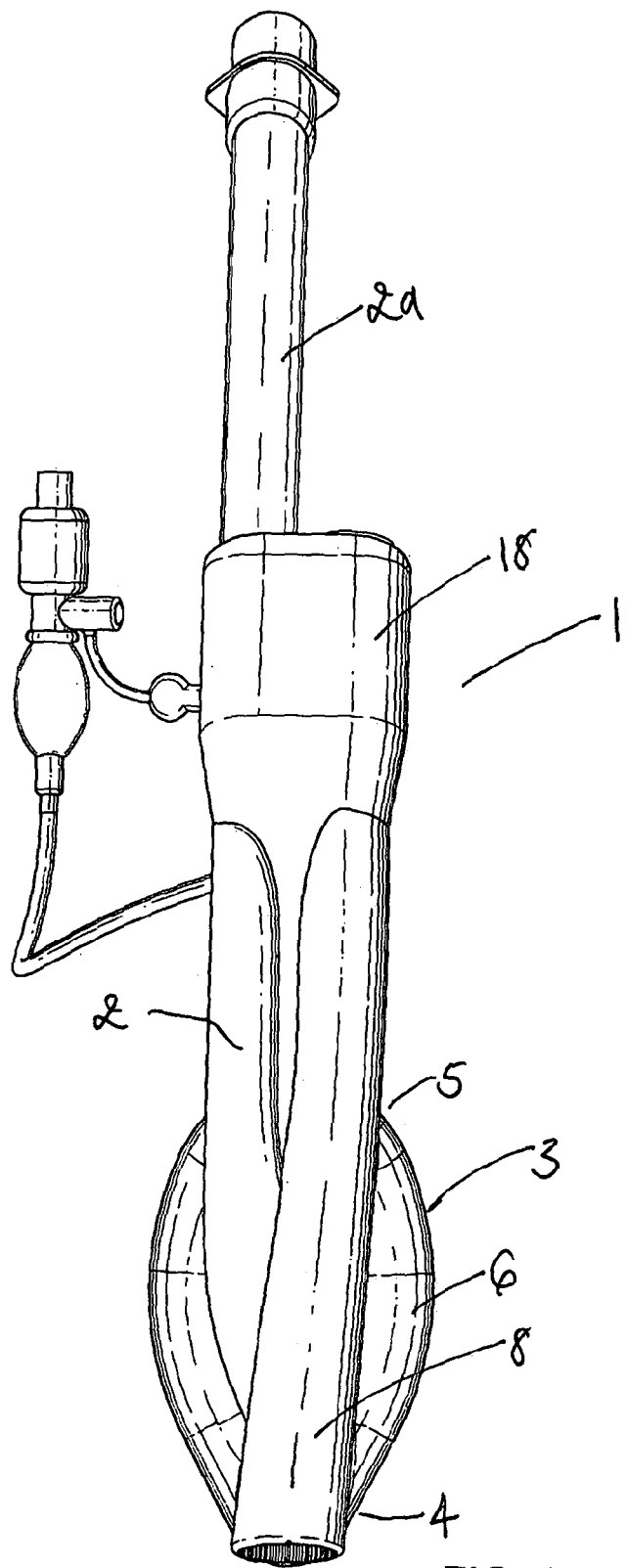
FIG. 12 is a plan view of the device of FIG. 9.

Referring now to FIG. 8, a variation of the device of FIGS. 1 to 7 is illustrated. In this variation the conduit 8 is provided with a bite block 17 which can also include a connector to facilitate insertion of an endoscope.

Referring to now to FIGS. 9 to 20, there is illustrated a third embodiment of device 1 according to the invention. As can be seen from, in particular, FIGS. 10 to 13, the device 1 resembles the devices illustrated in FIGS. 1 to 8 in that it includes at least one airway tube 2 and a mask 3 carried at one end of the at least one airway tube, the mask 3 having a distal end 4 and a proximal end 5 and a peripheral formation 6 capable of conforming to, and of fitting within, the actual and potential space behind the larynx of the patient so as to form a seal around the circumference of the laryngeal inlet, the peripheral formation 6 surrounding a hollow interior space or lumen 7 of the mask 3 and the at least one airway tube 2 opening into the lumen 7 of the mask, the device further comprising a conduit 8 adapted for passage of a gastroscope into the oesophagus of a patient when the mask 3 is in place. The various details of materials and construction as described above may also be applied to this embodiment.

In this embodiment it can be seen that the airway tube 2 and the conduit 8 are both received in a part 18 which in this embodiment part 18 takes the form of a biteblock 18. Biteblock 18 is an integrally molded plastics part and is formed with two bores, one each to accommodate the airway tube 2 and the conduit 8. As an alternative, it will be appreciated that the bite block 18 can be formed integrally with one or both of the airway tube 2 and conduit 8. The bite block 18 has upper and lower (in use) bite surfaces 18a, 18b which may be formed integrally with relatively softer material or soft material inserts in order to prevent damage to the teeth of a patient when the device 1 is in use. The bite block 18 has proximal and distal ends 19a, 19b and is provided at its distal end 19b with tapered section 19c to aid in inserting the device 1. As can be seen from FIG. 18, at its proximal end 19a, the bite block 18 has a generally flat face 20 with bores 20a and 20b. An airway tube extension 2a can be attached at bore 20b as illustrated, or alternatively a relatively longer airway tube 2 can be utilised which passes from the mask portion through the bite block 18 and extends out the other side. As will be appreciated, the bite block 18 not only serves to prevent puncturing of both the airway tube 2 and conduit 8, but also imparts structural integrity and rigidity to the device 1, keeping the airway tube 2 and conduit 8 in position relative to each other and the other components of the device 1.

Figure 13:
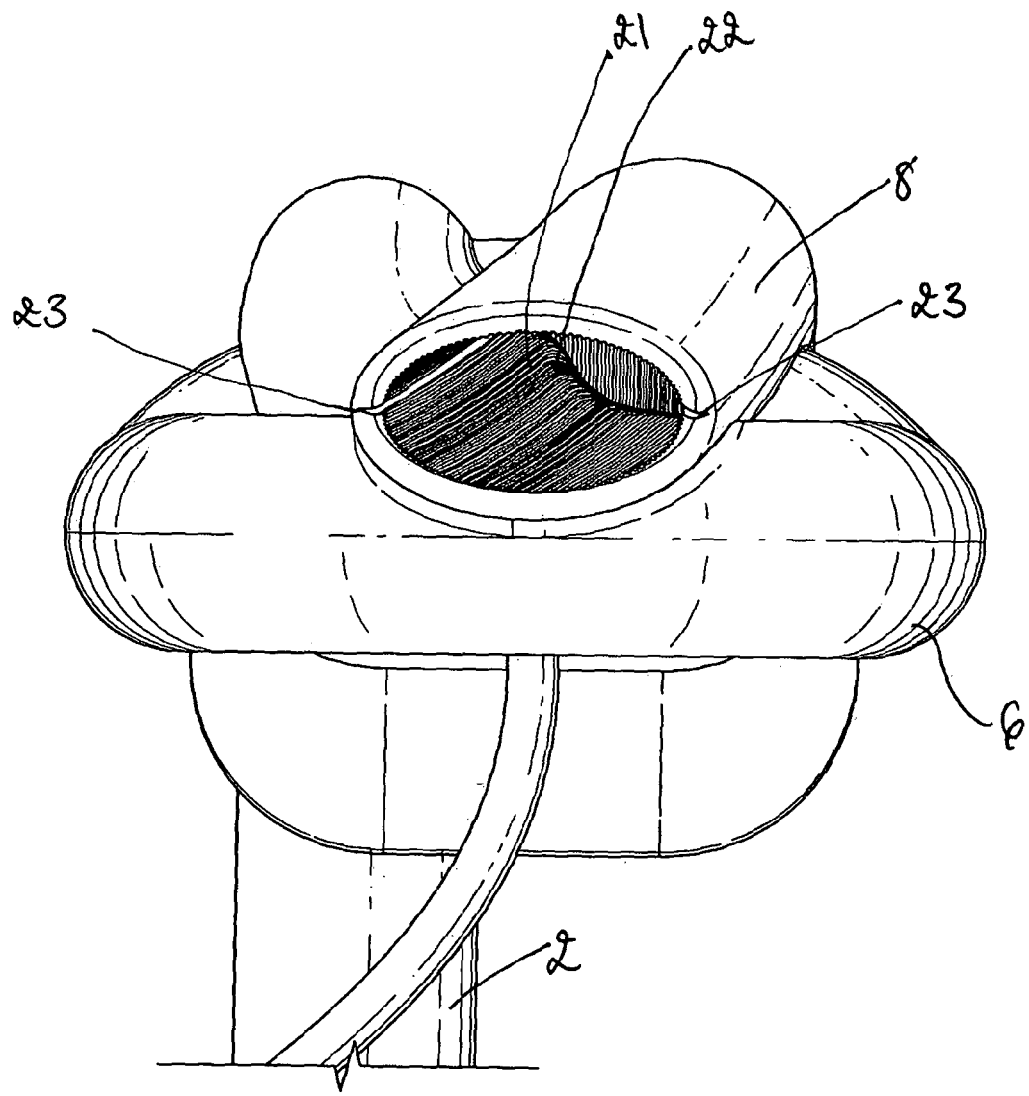
FIG. 13 is a front view of the device of FIG. 9.
Figure 14:
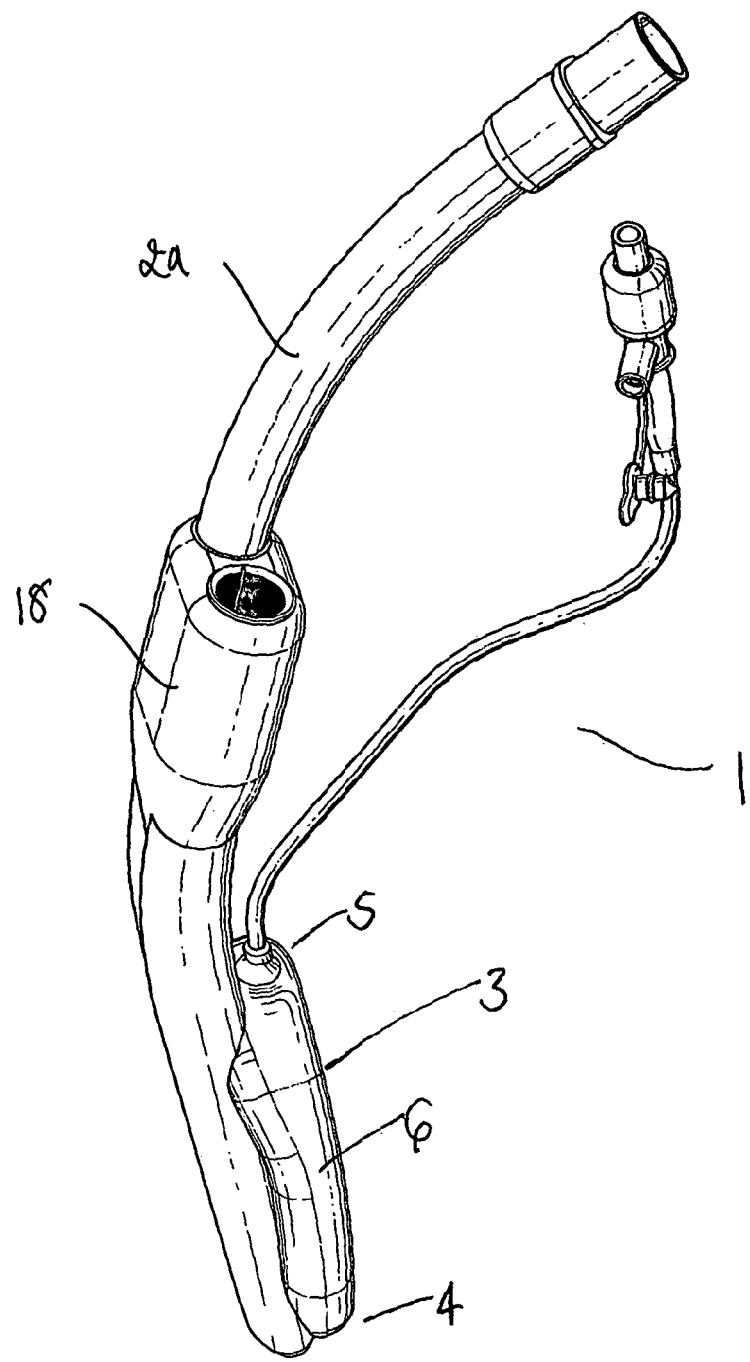
FIG. 14 is a left rear three quarter view view of the device of FIG. 9.
Figure 15:
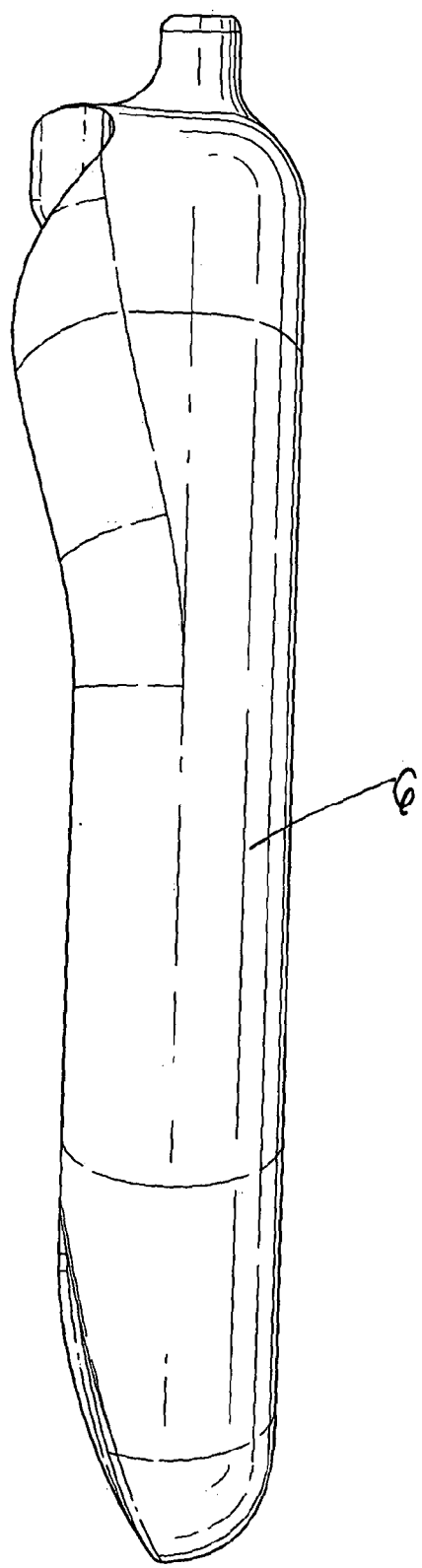
FIG. 15 is a side view of a part of view of the device of FIG. 9.
Figure 16:
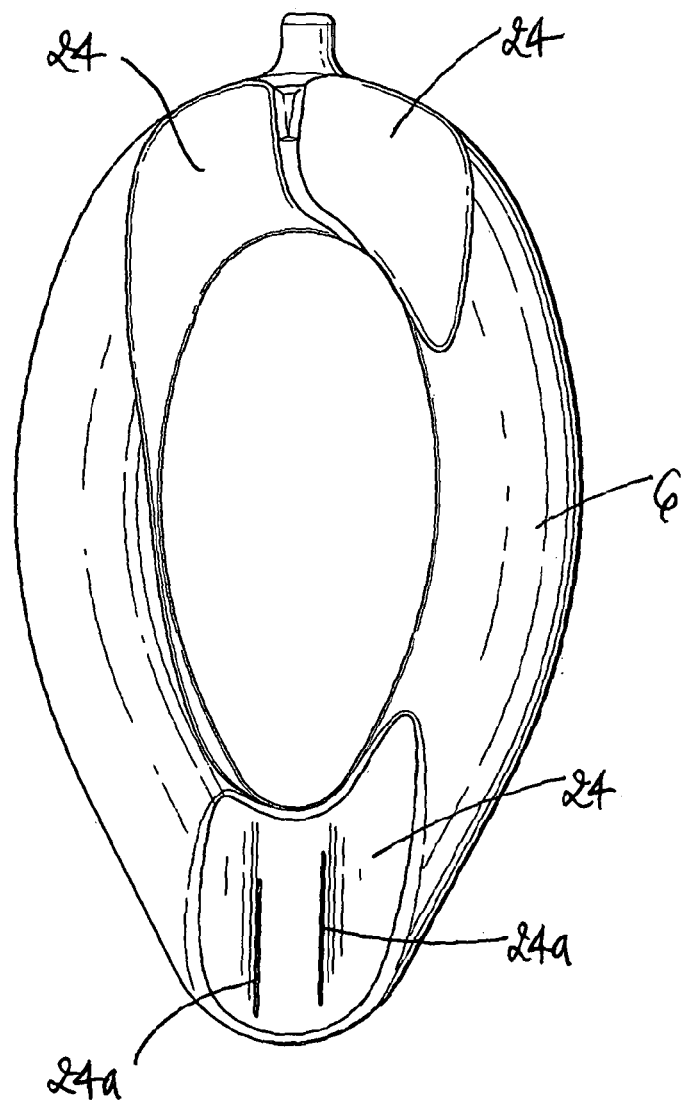
FIG. 16 is a plan view of the part of FIG. 15.

Referring now to FIG. 13, it can be seen that the conduit 8 has an oval section to assist in insertion of the device 1 and also has an internal surface 21 provided with means to reduce friction 22, in the form of longitudinally extending ridges. The ridges 22 combine to form a much smaller internal surface area than would otherwise be provided by a smooth internal bore and thus friction between the conduit 8 and an inserting endoscope is reduced. The ridges may extend for the entire length of the conduit, or a significant portion thereof. As an additional or alternative friction reducing means the conduit 8 can be provided with a polysiloxane coating for lubricity. It will also be seen from FIG. 13 that the internal surface of the conduit 8 is provided with two opposing longitudinally extending channel 23 which here resemble "V" shaped cuts. These channels serve as hinge points allowing the conduit 8 to be more easily compressed, or expanded, top to bottom as viewed in FIG. 13, to aid in insertion of the device 1 and also to aid in passing an endoscope through the conduit 8.

Figure 17:
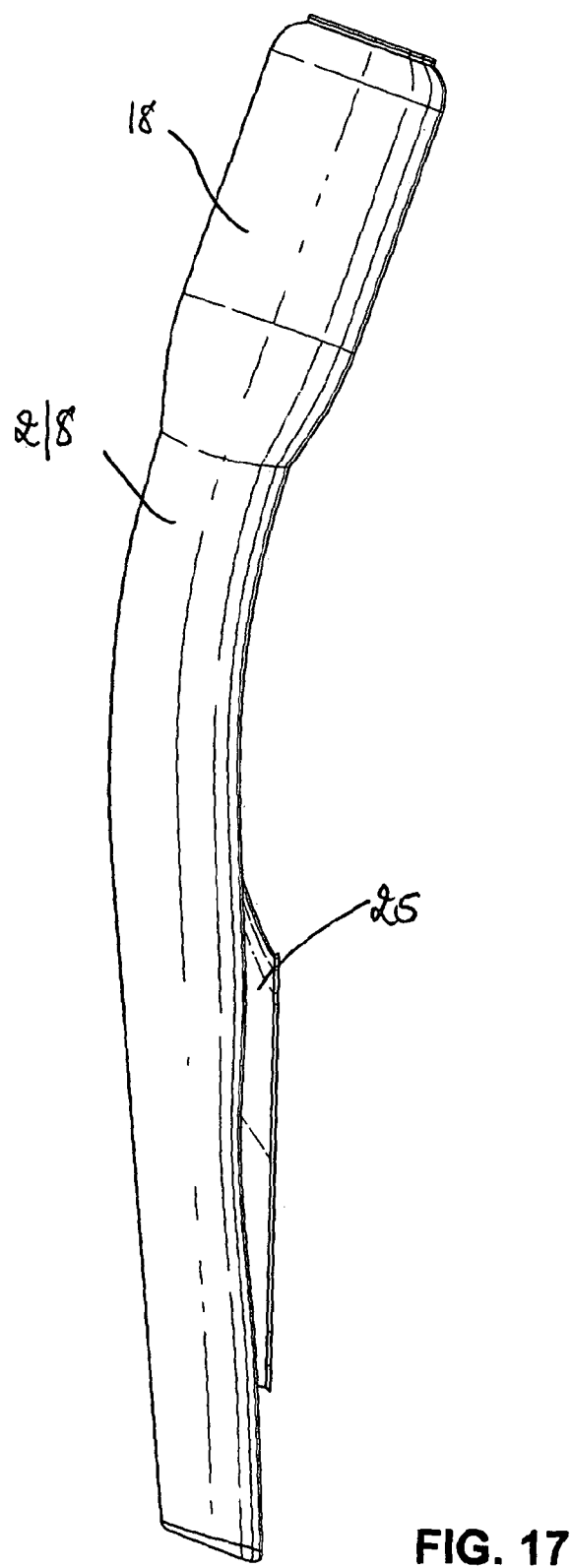
FIG. 17 is a side view of a further part of the device 9.
Figure 18:
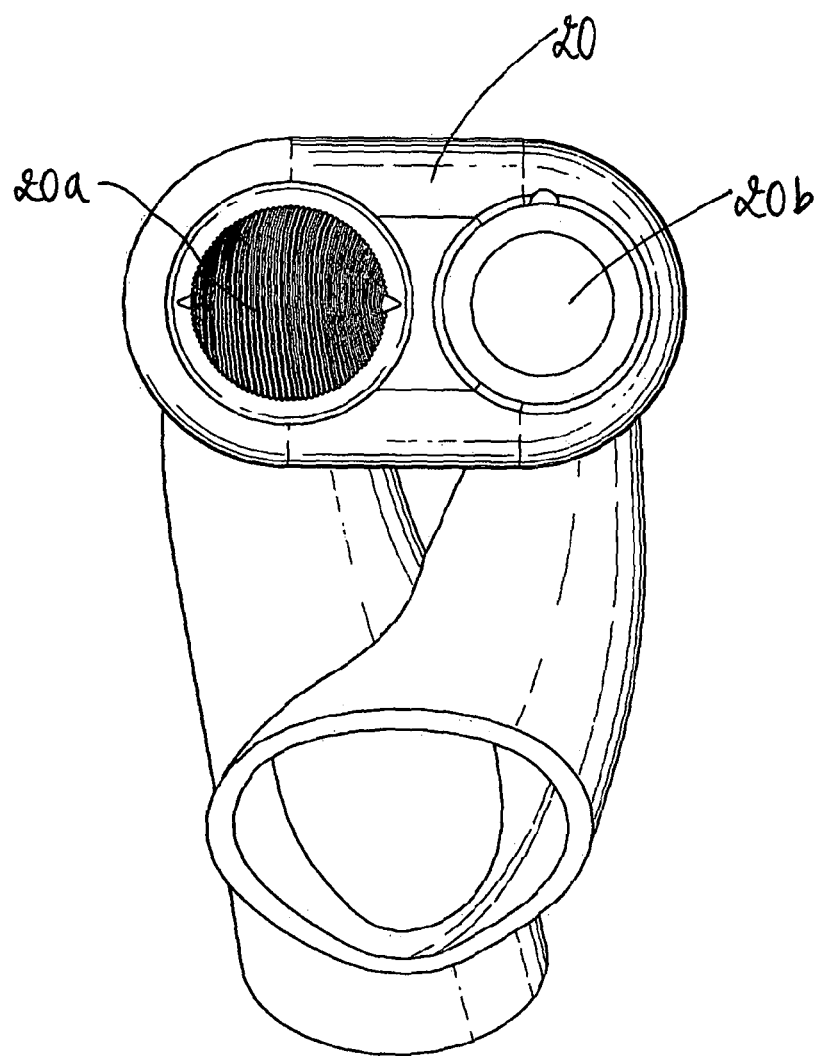
FIG. 18 is a rear view of the part of FIG. 17.
Figure 19:
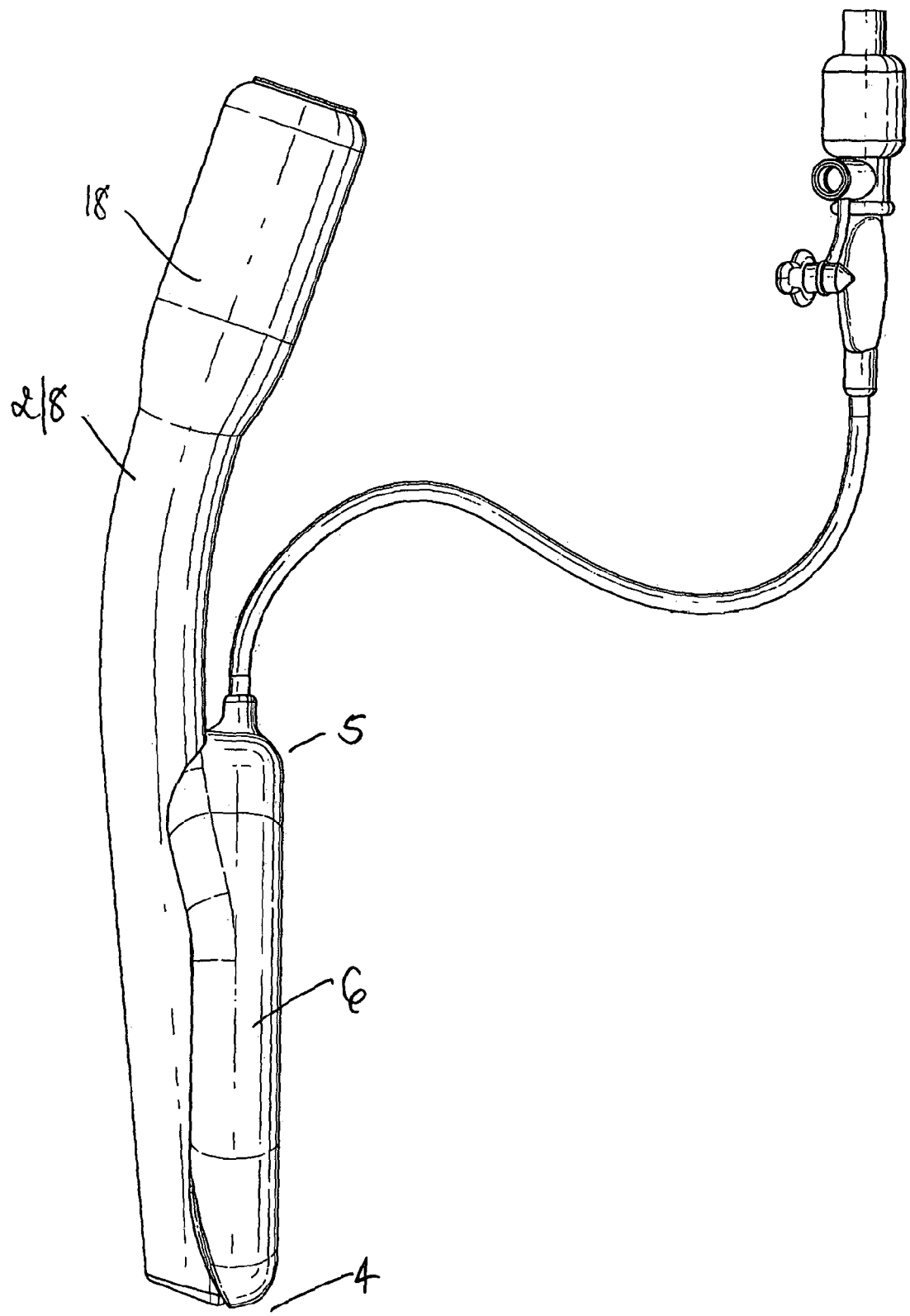
FIG. 19 is a left side view of the parts of FIGS. 15 and 17 in an assembled condition.
Figure 20:
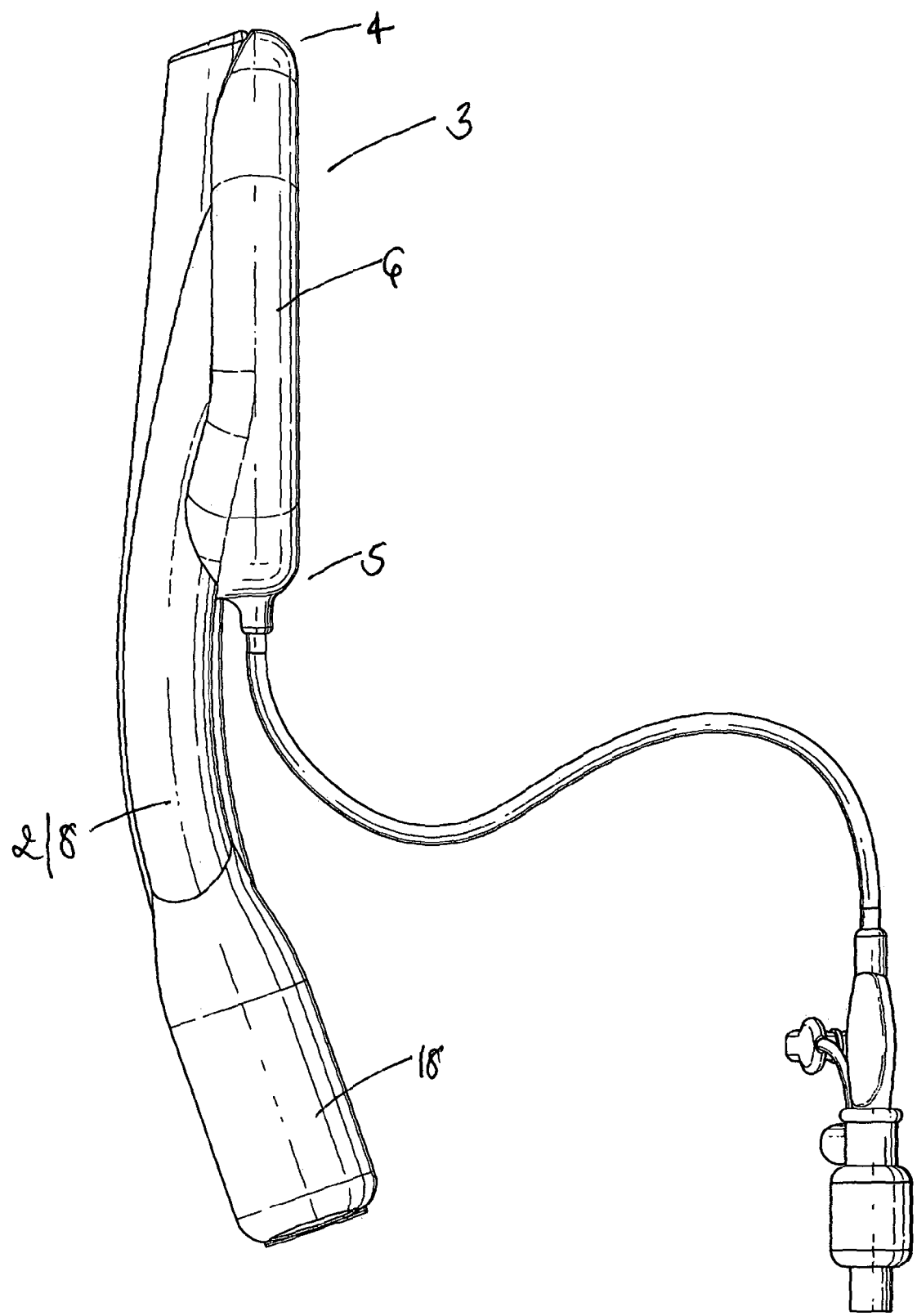
FIG. 20 is right side view of the assembly of FIG. 19.
Figure 21:
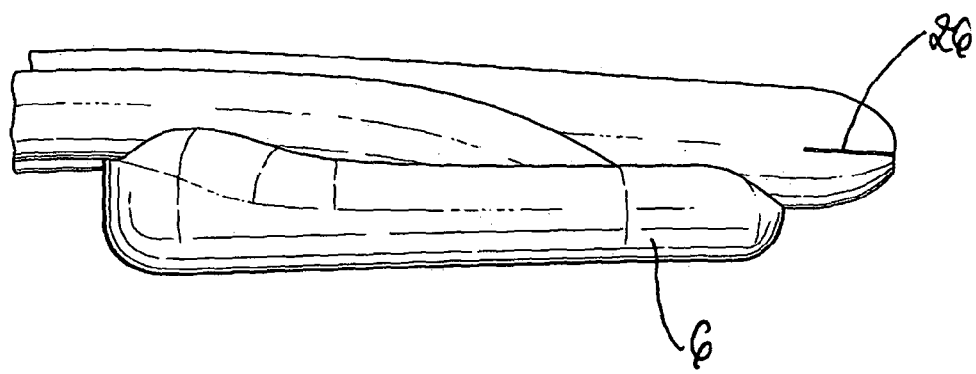
FIG. 21 is a side view of a part of a further embodiment of device according to the invention in a first position.
Figure 22:
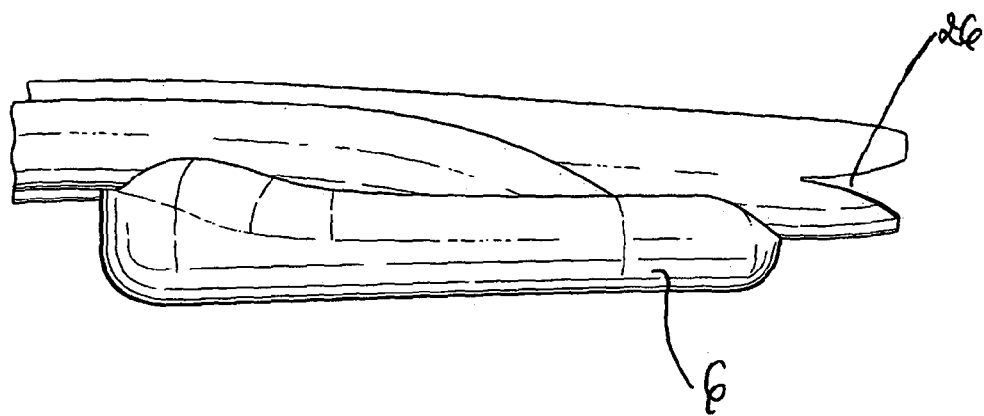
FIG. 22 is a view of the part of FIG. 21 in a second position.
Figure 23:
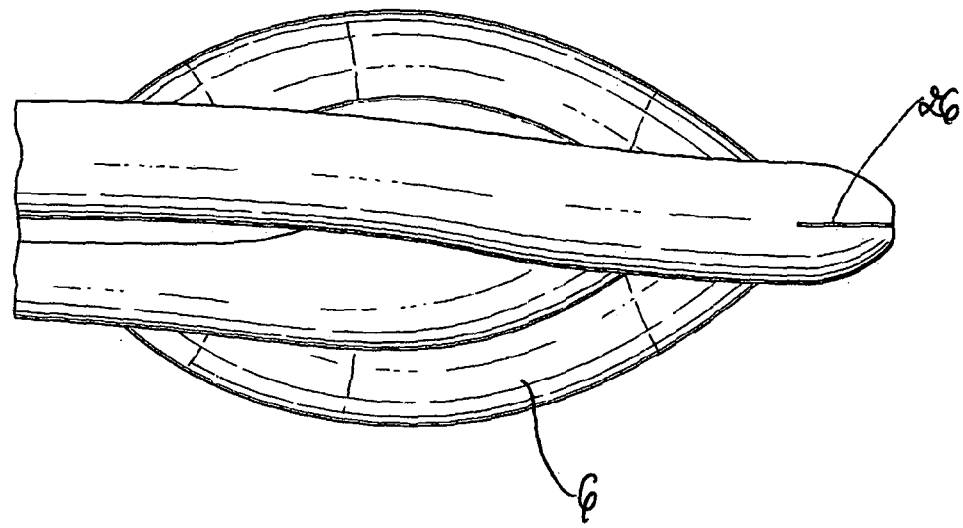
FIG. 23 is a plan view of the part of FIG. 21 in the first position.
Figure 24:
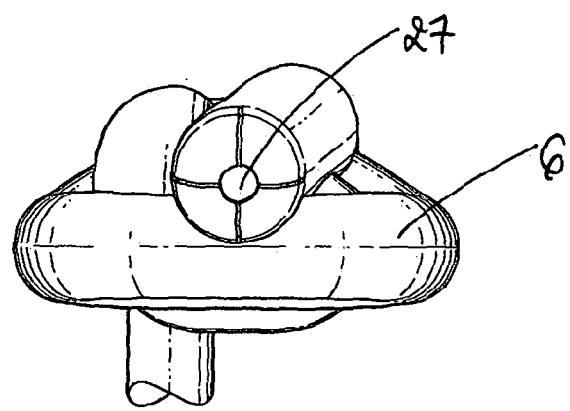
FIG. 24 is a front view of the part of FIG. 21 in the first position.
Figure 25:
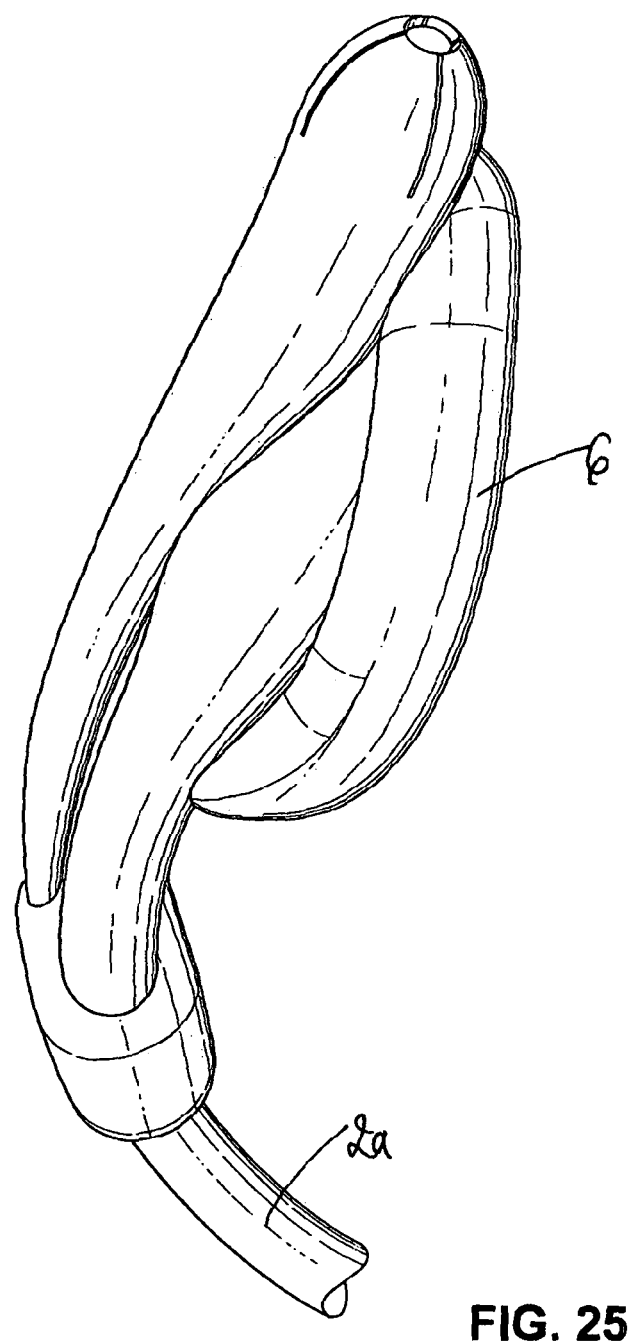
FIG. 25 is a front perspective view of a device according to the invention incorporating the part shown in FIG. 21.
Figure 26:
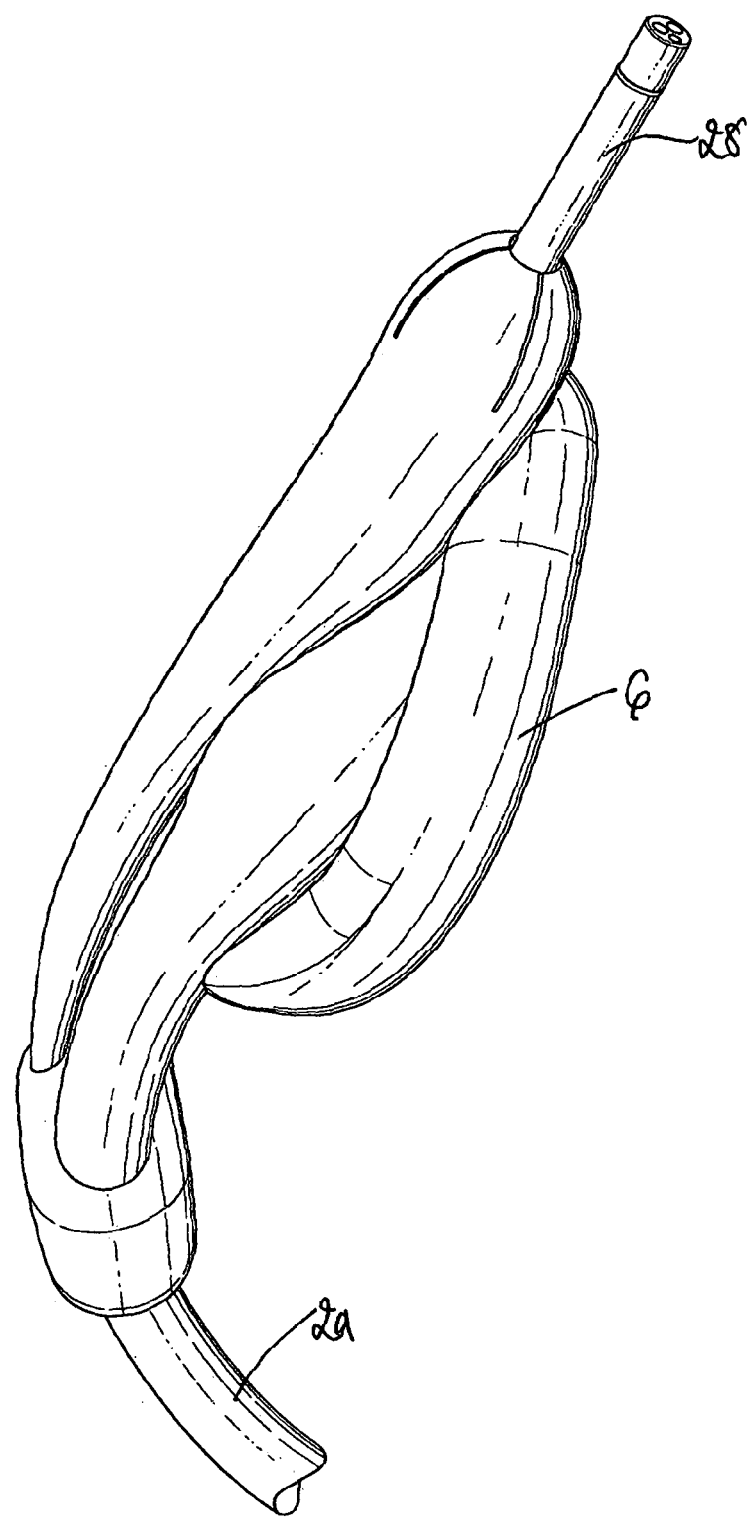
FIGS. 26 and 27 are front perspective views of the device of FIG. 25 in use with a first endoscope.
Figure 27:
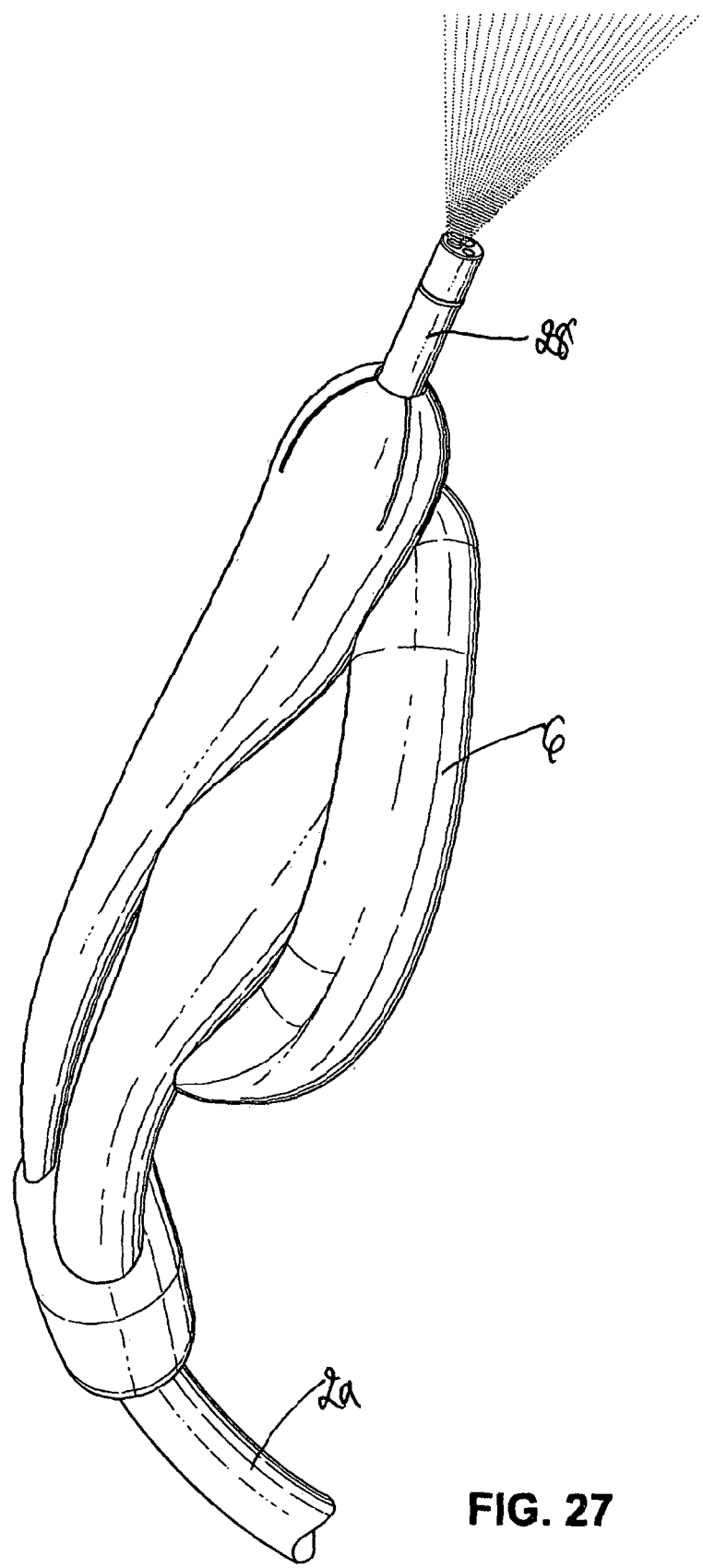
Figure 28:
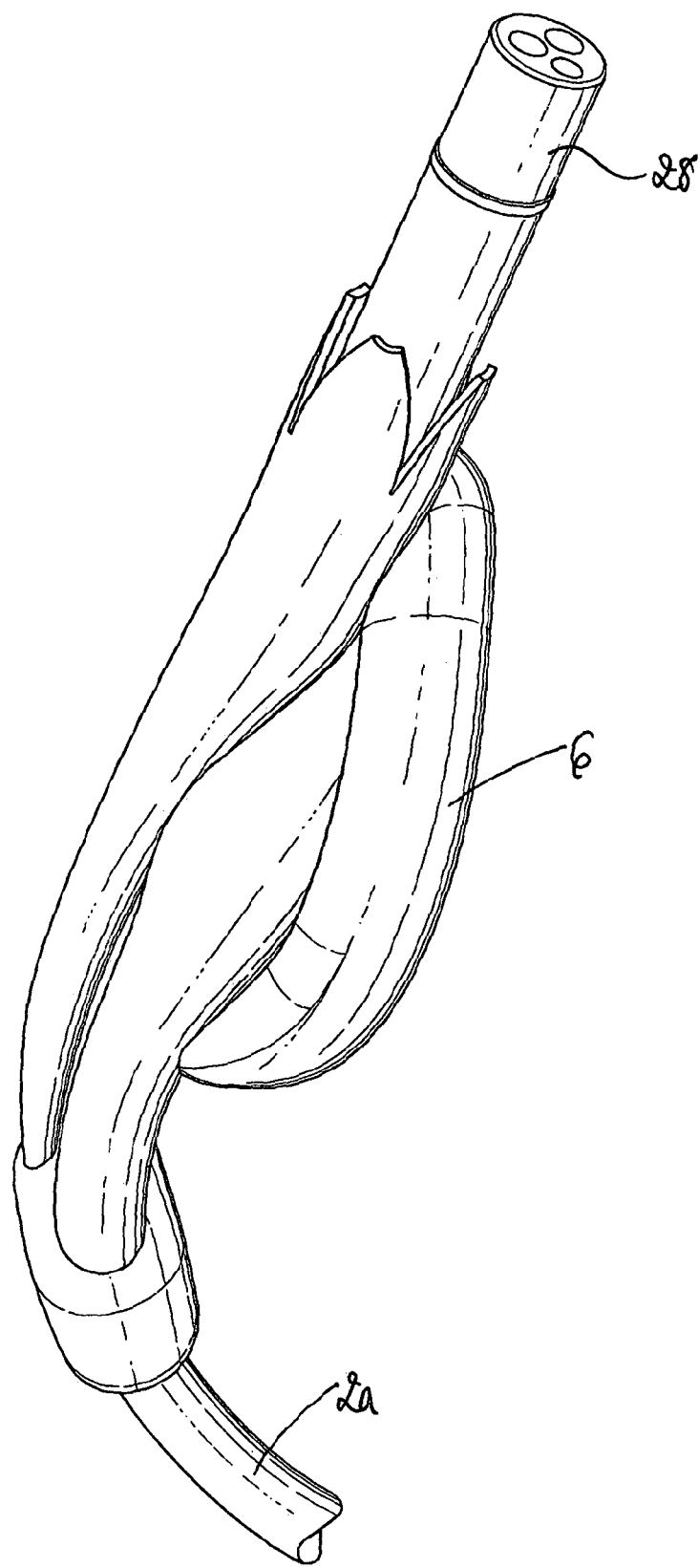
FIGS. 28 and 29 are front perspective views of the device of FIG. 25 in use with a second endoscope.
Figure 29:
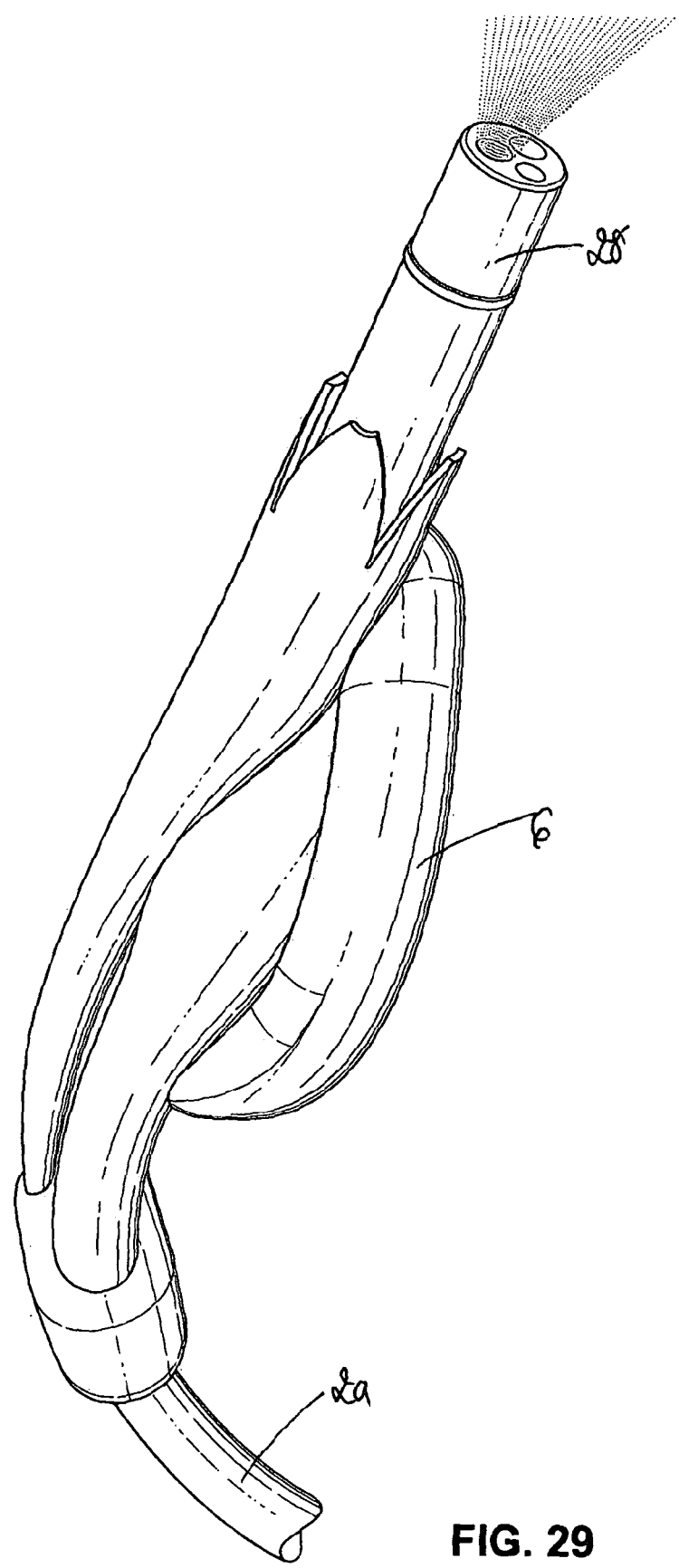

FIGS. 15 to 20 illustrate how the device 1 may advantageously be formed. As can be seen, the device 1 is comprised of three major parts, a cuff part 6, a combined airway tube and conduit assembly 2/8 which may be referred to as a backplate, and an inflation line. The cuff part 6 illustrated in FIGS. 15 and 16 may be integrally moulded from a plastics material or silicone. It is generally of conventional shape as known in the art, but includes curved mounting surfaces 24 with adhesive ridges 24a on its upper, in use, side. The airway tube and conduit assembly 2/8 illustrated in FIGS. 17 and 18 may be integrally formed or may include parts that are preformed, finished and assembled. As will be appreciated, the assembly shown in FIG. 18 is unfinished such that the airway tube 2 and conduit 8 are longer in extent than in the finished assembly shown in FIG. 17. Referring to FIG. 17, it can be seen that the airway tube 2 terminates in a downwardly directed flared end part 25 below the level of the conduit 8 as viewed that mates with mounting surfaces 24 of the cuff part 6. An inflation line can then be attached to the cuff part 6 by any suitable means. As illustrated, it is preferred that the end of the conduit 8 is cut rearwardly relative to a plane perpendicular to its longitudinal axis at an angle of 20 degrees.

FIGS. 21 to 29 illustrate a fourth embodiment of device according to the invention the invention. As with previously described embodiments, the device 1 consists of at least one airway tube 2 and a mask 3 carried at one end of the at least one airway tube, the mask 3 having a distal end 4 and a proximal end 5 and a peripheral formation 6 capable of conforming to, and of fitting within, the actual and potential space behind the larynx of the patient so as to form a seal around the circumference of the laryngeal inlet, the peripheral formation 6 surrounding a hollow interior space or lumen 7 of the mask 3 and the at least one airway tube 2 opening into the lumen 7 of the mask, the device further comprising a conduit 8 adapted for passage of a gastroscope into the oesophagus of a patient when the mask 3 is in place. The various details of materials and construction as described above may also be applied to this embodiment.

As will be appreciated, the major difference between this device and those previously described is the configuration of the distal end of the conduit 8. In this embodiment the distal end of the conduit 8 tapers and is provided with means 26 to allow expansion of the outlet 27. In this embodiment the means 26 takes the form of four slits in the wall of the conduit 8 that extend from the outlet back a distance that is sufficient to allow the outlet to expand substantially in the range of from 5 mm to at least 15 mm. Thus, in a first position illustrated in FIGS. 26 and 27 the outlet 27 is sufficiently large in diameter to accommodate an endoscope 28 of approximately 5 mm diameter without expansion, whereas in FIGS. 28 and 29, the outlet is shown in a second position wherein it is expanded to accommodate an endoscope of approximately 15 mm diameter. Although endoscopes currently in use are no larger in diameter than 15 mm the invention can thus accommodate larger scopes in future.

Thus, it has been demonstrated that the present invention provides a device that enables the safe and accurate insertion of an endoscope 28 into the oesophagus of a patient, whilst at the same time establishing an airway and protecting the airway from vomiting or regurgitation that may occur upon insertion of an endoscope.

The invention claimed is:

1. An endoscopy device for facilitating the use of an endoscope in a patient, comprising:
    a single airway tube, and a mask carried at one end of the single airway tube, the mask having a distal end and a proximal end and a peripheral formation having a distal end and a proximal end, the peripheral formation capable of conforming to, and of fitting within, the actual and potential space behind the larynx of the patient so as to form a seal around a circumference of the laryngeal inlet, the peripheral formation surrounding a hollow interior space or lumen of the mask and the single airway tube opening into the hollow interior space or lumen of the mask, a conduit adapted for passage of the endoscope into the oesophagus of the patient when the mask is in place in the patient, the conduit having a distal end and a proximal end, wherein the distal end of the conduit is substantially adjacent to the distal end of the peripheral formation and extends to the distal end of the peripheral formation, wherein the conduit has a length that, in use, extends from the distal end of the mask, passes through the mouth of a patient and emerges between the teeth of the patient, and wherein the single airway tube has a diameter smaller than a diameter of the conduit, and wherein the device comprises a proximal end and a distal end, wherein a major axis is provided therebetween, and wherein the conduit is provided at an angle, such that a longitudinal axis of the conduit is offset, along the entire length of the conduit, relative to a midline with respect to the major axis of the device.

2. The endoscopy device according to claim 1, wherein the device is adapted to minimise the frictional contact between an inside surface of a wall of the conduit and the endoscope when inserted therein.

3. The endoscopy device according to claim 2, wherein the device is provided with means to reduce the surface area of the wall of the conduit in contact with the endoscope when inserted therein.

4. The endoscopy device according to claim 3, wherein the means comprises a plurality of longitudinally extending ridges.

5. The endoscopy device according to claim 1, wherein the diameter of the conduit is between about 5 and 25 mm, and wherein a radial wall thickness of the conduit is between about 1 and 2 mm.

6. The endoscopy device according to claim 3, wherein the conduit comprises a plurality of bores formed in its wall.

7. The endoscopy device according to claim 5, wherein the conduit comprises a plurality of channels formed in its wall.

8. The endoscopy device according to claim 1, wherein the conduit comprises a silicone material, and has a durometer hardness of between 60 and 70 Shore.

9. The endoscopy device according to claim 1, wherein the peripheral formation is an inflatable cuff having a distal end and a proximal end.

10. The endoscopy device according to claim 1, wherein the mask comprises a backplate.

11. The endoscopy device according to claim 1, wherein the single airway tube and/or conduit include a bite block.

12. The endoscopy device according to claim 1, wherein the distal end of the conduit is provided at an angle α of about 10 to 15 degrees to a horizontal plane, wherein the horizontal plane is perpendicular to the major axis of the device when the device is in a substantially linear conformation.

13. The endoscopy device according to claim 1, wherein the conduit and the single airway tube are maintained in a configuration such that they are separate from one another.

14. The endoscopy device according to claim 1, wherein the conduit and the single airway tube are connected to one another.

15. The endoscopy device according to claim 1, including means to allow expansion of an outlet of the conduit.

16. The endoscopy device according to claim 15, wherein the means comprises slits adjacent the outlet of the conduit.

17. The endoscopy device according to claim 1, wherein the distal end of the conduit is provided at an angle α of about 45 degrees to a horizontal plane, wherein the horizontal plane is perpendicular to the major axis of the device when the device is in a substantially linear conformation.

18. The endoscopy device according to claim 17, wherein the diameter of the conduit is between about 5 and 25 mm, and wherein a radial wall thickness of the conduit is between about 1 and 2 mm.

* * * * *